United States Patent [19]
Melnick et al.

[11] Patent Number: 6,063,562
[45] Date of Patent: May 16, 2000

[54] IN VITRO METHOD FOR PREDICTING THE EVOLUTIONARY RESPONSE OF HIV PROTEASE TO A DRUG TARGETED THEREAGAINST

[75] Inventors: Laurence M. Melnick, Watertown; Donald L. Heefner, Hudson, both of Mass.

[73] Assignee: Sepracor, Inc., Marlborough, Mass.

[21] Appl. No.: 08/420,003

[22] Filed: Apr. 10, 1995

Related U.S. Application Data

[63] Continuation-in-part of application No. 08/307,322, Sep. 16, 1994, abandoned.

[51] Int. Cl.[7] .................................................... C12Q 1/70
[52] U.S. Cl. ................................ 435/5; 435/7.1; 435/7.2; 435/7.6; 435/7.92; 435/23; 435/974; 435/975
[58] Field of Search .................................... 435/5, 7.1, 7.2, 435/7.6, 7.92, 23, 974, 975

[56] References Cited

U.S. PATENT DOCUMENTS

| | | | |
|---|---|---|---|
| 5,223,408 | 6/1993 | Goeddel et al. | 435/69.3 |
| 5,223,409 | 6/1993 | Ladner et al. | 435/69.7 |
| 5,258,289 | 11/1993 | Davis et al. | 424/805 |
| 5,288,514 | 2/1994 | Ellman | 435/4 |
| 5,300,425 | 4/1994 | Kauvar | 435/7.9 |

FOREIGN PATENT DOCUMENTS 2276621  10/1994  United Kingdom.

OTHER PUBLICATIONS

Chow et al., "Use of evolut. limit. of HIV–1 multidrug resist. to optimize therapy," Nature, 1993; 361:650–4.
Chow et al., "HIV–1 error revealed," Nature, 1993; 364:679.
Emini et al., "HIV and multidrug resistance," Nature, 1993; 364:679.
Tisdale et al., "Rapid in vitro select. of human immunodef. virus type 1 resistant to 3'–thiacytidine inhib. due to a mutation in the YMDD region of reverse transcript.," Proc. Natl. Acad. Sci. USA, 1993; 90:5653–6.
Taddie et al., "Genetic Charact. of the Vaccinia Virus DNA Polymerase: Identific. of Point Mutations Conferring Altered Drug Sensit. and Reduced Fidelity," Journal of Virology, 1991; 65(2):869–79.
Johnston et al., "Present Status and Future Prospects for HIV Therapies," Science, 1993; 260:1286–93.
Richman, "HIV Drug Resistance," Annu. Rev. Pharmacol. Toxicol., 1993; 32:149–64.
Meyerhans et al., "Temp. Fluctutations in HIV Quasispecies In Vivo Are Not Reflected by Sequen. HIV Isolations," Cell, 1989; 58:901–10.
Wain–Hobson, "The fastest genome evolution ever described: HIV variation in situ," Current Opinion in Genetics and Development, 1993; 3:878–83.
Honess et al., "Single Mutations at Many Sites within the DNA Polymerase Locus of Herpes Simplex Viruses Can Confer Hypersens. to Aphidicolin and Resistance to Phosponoacetic Acid," J. gen. Virol., 1984; 65:1–17.

Lacey et al., "Anal. of mutations in the thymidine kinase genes of drug–resist. varicella–zoster virus popul. using the polymerase chain reaction," Journal of General Virology, 1991; 72:623–30.
Alper, "Drug Discovery on the Assembly Line," Science, 264:1399–1401 (Jun. 3, 1994).
Matthews et al., "In Vitro Mutagen. of the Herpes Simplex Virus Type 1 DNA Polymerase Gene Results in Altered Drug Sensitiv. of the Enzyme," Journal of Virology, 1989; 63(11):4913–8.
Roberts et al., "Rational Design of Peptide–Based HIV Proteinase Inhibitors," Science, 1990; 248:358–61.
Handwerger et al., "Alterat. in Penicillin–Binding Proteins of Clinic. and Laboratory Isolated of Path. *Streptococcus pneumoniae* with Low Levels of Penicillin Resistance," The Journal of Infectious Diseases, 1986; 153(1):83–9.
Smith et al., "Resumption of Virus Production after Human Immunodef. Virus Infection of T Lymphocytes in the Presence of Azidothymidine," Journal of Virology, 1987; 61(12):3769–73.
Larder et al., "Zidovudine–Resistant Human Immunodef. Virus Selected by Pass. in Cell Cult.," Journal of Virology, 1991; 65(12):5232–6.

(List continued on next page.)

*Primary Examiner*—Jeffrey Stucker
*Attorney, Agent, or Firm*—Heslin & Rothenberg, P.C.

[57] ABSTRACT

An in vitro method for predicting the identity of distinct, first-generation, drug-resistant, biologically-active, HIV protease mutants that may emerge in vivo in response to a drug targeted thereagainst. In a preferred embodiment, the in vitro method comprises the steps of (a) preparing, in the presence of the drug, a comprehensive library of all first-generation mutants of the protease differing therefrom by at least one and preferably no more than three amino acid substitutions, each of the protease mutants being generated as part of a polyprotein with the HIV reverse transcriptase protein; (b) isolating, in vitro, first-generation, drug-resistant, biologically-active, mutant proteases from said library by assaying for biological activity of the reverse transcriptase protein; and (c) identifying the distinct, first-generation, biologically-active, mutant proteases so isolated. The present invention also relates to an in vitro method for evaluating the efficacy of a drug against a biologically-active mutant or wild-type form of HIV protease, said method comprising the steps of (a) providing a mutant polyprotein, said mutant polyprotein including a biologically-inactive mutant form of the protease linked to HIV reverse transcriptase by one or more sites cleavable by the biologically-active or wild-type form of the protease; (b) adding the drug to the mutant polyprotein; (c) then, adding the biologically-active or wild-type form of the protease to the mutant polyprotein; and (d) then, assaying for the presence of biological activity for reverse transcriptase, whereby the presence of reverse transcriptase activity indicates that the drug is not efficacious against the biologically-active mutant or wild-type form of the protease tested. The present invention further relates to a kit for evaluating the efficacy of a drug against a biologically-active mutant or wild-type form of HIV protease.

14 Claims, 10 Drawing Sheets

OTHER PUBLICATIONS

Tanouye, "Pharmaceutical Consortium to Begin Clinical Trials of Comb. AIDS Drugs," Wall Street Journal (Apr. 14, 1994).

Larder et al., "Infect. potential of human immunodef. virus type 1 reverse transcriptase mutants with altered inhib. sensit.,"Proc. Natl. Acad. Sci. USA, 1989; 86:4803–7.

Kageyama et al., "In Vitro Inhib. of Human Immunodef. Virus (HIV) Type 1 Replication by $C_2$ Symmetry–Based HIV Protease Inhib. as Single Agents or in Combin.," Antimicrobial Agents and Chemotherapy, 1992; 36(5):926–33.

Ho et al., "Characterization of Human Immunodef. Virus Type 1 Variants with Increased Resist. to a $C_2$–Symmetric Protease Inhib.," Journal of Virology, 68(3):2016–20 (Mar. 1994).

Neu, "The Crisis in Antibiotic Resistance," Science, 1992; 257:1064–73.

Mohri et al., "Quantitation of zidovudine–resistant human immunodef. virus type 1 in the blood of treated and untreated patients," Proc. Natl. Acad. Sci. USA, 1993; 90:25–9.

Barbas III et al., "Semisynth. combinatorial antibody libraries:A chem soln. to the diversity prob.," Proc.Natl.Acad-.Sci.USA,1992;89:4457–61.

Amberg et al., "SurfZAP™ Vector*:Linking Phenotype to Genotype for Phagemid Display Libraries," Strategies in molecular biology, 6:2–4, published prior to the filing of the present application.

McCafferty et al., "Phage antibod.:filamentous phage displaying antibody variable domains," Nature, 1990; 348:552–4.

Matthews et al., "Substrate Phage:Selection of Protease Substrates by Monovalent Phage Display," Science, 1993; 260:1113–7.

Fields et al., "A novel genetic system to detect protein–protein interactions," Nature, 1989; 340:245–6.

Saag et al., "Extensive variation of human immunodeficiency virus type–1 in vivo," Nature, 1988; 334:440–4.

Nashed et al., "Continuous Spectrophotometric Assay for Retroviral Proteases of HIV–1 and AMV," Biochemical and Biophysical Research Communications, 1989; 163(2):1079–85.

Richards et al., "Sensitive, Soluble Chromogenic Substrates for HIV–1 Proteinase," The Journal of Biological Chemistry, 1990;265(14):7733–6.

Neu, "Quinolone Antimicrobial Agents," Annu. Rev. Med., 1992; 43:465–86.

Fasching et al., "gyrA Mutations in Ciprofloxacin–Resistant, Methicillin–Resistant *Staphylococcus aureus* from Indiana, Minnesota, and Tennessee," The Journal of Infectious Diseases, 1991; 164:976–9.

Larder et al., "Zidovudine resistance predicted by direct detection of mutations in DNA from HIV–infected lymphocytes," AIDS, 1991, 5:137–44.

Boucher et al., "Ordered Appearance of Zidovudine Resistance Mutations during Treatment of 18 Human Immunodeficiency Virus–Positive Subj.," The Journal of Infectious Diseases, 1992; 165:105–10.

Lopez–Galindez et al., "Charact. of genetic variation and 3'–azido–3'–deoxythymidine–resistance mutations of human immunodef. virus by the RNase A mismatch cleavage method," Proc. Natl. Acad. Sci. USA, 1991; 88:4280–4.

Nunberg et al., "Viral. Resist. to Human Immunodef. Virus Type 1–Spec. Pyrid. Rev. Transcr. Inhib.," Journal of Virology,1991;65(9):4887–92.

Dueweke et al., "A mutation in reverse transcriptase of bis(heteroaryl)piperazine–resistant human immunodef. virus type 1 that confers increased sensitivity to other nonnucleoside inhib.," Proc. Natl. Acad. Sci. USA, 1993; 90:4713–7.

Banerjee et al., "inhA, a Gene Encoding a Target for Isoniazid and Ethionamide in *Mycobacterium tuberculosis*," Science, 263:227–30 (Jan. 14, 1994).

Richman et al., "Detection of Mutations Associated with Zidovudine Resist. in Human Immunodef. Virus by Use of the Polymerase Chain Reaction," The Journal of Infectious Diseases, 1991; 164:1075–81.

Reynolds, "Resistance of the Antibiotic Target Site," British Medical Bulletin, 1984; 40(1):3–10.

Debyser et al., "Kinetics of Diff. Human Immunodef. Virus Type 1 Rev. Transcriptases Resist. to Human Immunodef. Virus Type 1–Specific Rev. Transcriptase Inhibitors," Molecular Pharmacology, 1993; 43:521–6.

Pauwels et al., "Potent and highly select. human immunodef. virus type 1 (HIV–1) inhibition by a series of α–anilinophenylacetamide deriv. targeted at HIV–1 rev. transcriptase," Proc. Natl. Acad. Sci. USA, 1993; 90:1711–5.

Gu et al., "Novel Mutation in the Human Immunodef. Virus Type 1 Rev. Transcript. Gene That Encodes Cross–Resist. to 2',3'–Dideoxyinosine and 2',3'–Dideoxycytidine," Journal of Virology, 1992; 66(12):7128–35.

Hedge et al., "Amino acid subst. that reduce the affinity of pencillin–binding protein 3 of *Escherichia coli* for cephalexin," Eur. J. Biochem., 1985; 151:111–21.

Spratt et al., "Penicillin–Binding Proteins of Gram–Negative Bact.," Reviews of Infectious Diseases, 1988; 10(4):699–711.

Sardana et al., "Funct. Anal. of HIV–1 Rev. Transcript. Amino Acids Involved in Resist. to Mult. Nonnucleoside Inhibitors," J. Biol. Chem., 1992; 267:17526–30.

Hedge et al., "Resistance to β–lactam antibiotics by re–modelling the active site of an *E. coli* penicillin–binding protein," Nature, 1985; 318:478–80.

Kaplan et al., "Selection of multiple human immunodeficiency virus type 1 variants that encode viral proteases with decreased sensitivity to an inhibitor of the viral protease," Proc. Natl. Acad. Sci. USA, 91:5597–601 (Jun. 1994).

Blair et al., "Amino Acids Determining Enzyme and Virus Sensitivity to HIV–1 Protease Inhibitors," J. Cell. Biochem., Suppl. 17E:74 (1993).

Loeb et al "Complete Mutagenesis of the HIV–1 Protease", *Nature*, vol. 340, Aug. 3, 1989, pp. 397–400.

Louis et al., "Autoprocessing of the HIV–1 protease using purified wild–type and mutated fusion proteins expressed at high levels in *Escherichia coli*," Eur. J. Biochem., 199:361–9 (1991).

IN VITRO METHOD FOR PREDICTING THE EVOLUTIONARY RESPONSE OF HIV PROTEASE TO A DRUG TARGETED THEREAGAINST

CROSS-REFERENCE TO RELATED APPLICATIONS

The present application is a continuation-in-part of U.S. patent application Ser. No. 08/307,322, filed Sep. 16, 1994, now abandoned, which is incorporated herein by reference.

FIELD OF THE INVENTION

It is well-known in the field of drug development that the pathogenicity of various microorganisms, such as viruses, bacteria and the like, may be eliminated, or at least controlled, by inactivating certain proteins essential to the survival and/or proliferation of the microorganisms. The present invention relates generally to an in vitro method for predicting the evolutionary response of such proteins to drugs targeted thereagainst. More specifically, the present invention relates to an in vitro method for predicting the evolutionary response to a drug of proteases, such as HIV protease, which are natively expressed as part of a polyprotein with a second protein that has a biological activity catalyzed by cleavage of the polyprotein by the protease. The method of the present invention may be used, for example, to identify, prior to clinical use, resistant biologically-active mutant forms of a protein which may emerge in response to the clinical use of a particular antimicrobial agent. In particular, the present method may be used to predict, prior to clinical use, all possible first-generation biologically-active resistant mutants which may emerge in response to the clinical use of a particular antimicrobial agent. In this manner, a cocktail of drugs including the antimicrobial agent and one or more auxiliary drugs effective against the aforementioned first-generation resistant mutant forms of the protein can be identified and, thereafter, used clinically to eliminate the evolutionary escape pathways of the protein. In a similar manner, a single drug can be identified which is effective against both the wild-type and the first-generation resistant mutant forms of the protein and which can be used clinically, instead of the aforementioned cocktail of drugs, to defeat drug resistance. The present method may also be used, for example, to evaluate, prior to clinical use, the ultimate efficacy of an inhibitor contemplated for use against the protein.

BACKGROUND OF THE INVENTION

One of the more significant scientific and technological advances for the past half-century has been the development of antimicrobial drugs, such as antibiotics and antiviral agents. The widespread availability of these drugs has saved millions of lives and has benefitted mankind in innumerable ways. The only limitation to the usefulness of such drugs has been the evolutionary development of drug-resistant pathogens.

Bacterial pathogens may become resistant to antibiotic drugs in a variety of ways, such as by mutating the target of the drug, by limiting uptake of the drug, or by destroying the drug. Often, the drug target is a protein necessary for the survival and/or proliferation of the pathogen, and resistance to the drug is conferred by means of one or more resistance-conferring mutations in the nucleic acid sequence which encodes the drug target, the resistance-conferring mutations resulting in mutant forms of the drug target in which the drug target loses its affinity for the drug targeted thereagainst while retaining its functionality.

The problem of widespread and ever-increasing bacterial resistance to antibiotics, which now poses a significant threat to public health, has recently been addressed by Harold C. Neu in "The Crisis in Antibiotic Resistance," Science, Vol. 257, pp. 1064–1073 (Aug. 21, 1992). As relayed by Neu, the extensive use of antibiotics over the past several decades has resulted in a proliferation of drug-resistant bacteria. As one example, Neu notes that, in 1941, virtually all strains of Staphylococcus aureus worldwide were susceptible to penicillin G whereas, today, in excess of 95% of S. aureus worldwide are resistant to penicillin, ampicillin, and the antipseudomonas penicillins. As another example, Neu notes that, in 1941, a therapy consisting of 10,000 units of penicillin administered four times a day for 4 days was sufficient to cure patients afflicted with pneumococcal pneumonia whereas, today, a patient could receive 24 million units of penicillin a day and still die of pneumococcal meningitis caused by Streptococcus pneumoniae.

Part of the problem of bacterial resistance to antibiotics stems from the manner in which such drugs have traditionally been developed and used. Typically, a first antibiotic is developed against a substantially uniform, static target (e.g., a single or a small number of pathogenic bacterial strains, a homogenous enzyme preparation, a uniform receptor preparation, or the like) and is then used against an ever-evolving, increasingly heterogeneous target until widespread resistance to the drug develops. Then, a second antibiotic is similarly developed against a resistant, yet similarly uniform and static, form of the target and is substituted for the first antibiotic until, in turn, widespread resistance to it develops. This sequence is usually perpetuated, as new drugs become available, over a period of years as evermore robust, heartier pathogens emerge in response to increasing selective pressure. Even though it has been appreciated that, in many instances, resistance to some drugs will develop over time, the consensus has been that new drugs will become available in the future to successfully combat resistant strains. Unfortunately, this has not always been the case, and the rate at which effective new antibiotics are currently being developed is slower than in the past.

Bacteria are not the only pathogenic microorganisms that have presented a problem to the medical community due to their ability to acquire resistance to drugs targeted thereagainst. Viruses, most notably the HIV virus, have presented a similar problem with respect to antiviral agents. See, e.g., H. Mohri et al., "Quantitation of zidovudine-resistant human immunodeficiency virus type 1 in blood of treated and untreated patients," Proc. Natl. Acad. Sci., U.S.A., Vol. 90, pp. 25–29 (1993); M. Tisdale et al., "Rapid in vitro selection of human immunodeficiency virus type 1 resistant to 3'-thiacytidine inhibitors due to a mutation in the YMDD region of reverse transcriptase," Proc. Natl. Acad. Sci., U.S.A., Vol. 90, pp. 5653–5656 (1993); and R. Yarchoan et al., "Challenges in the therapy of HIV infection," Clinical Perspectives, Vol. 14, pp. 196–202 (1993).

Margaret I. Johnston and Daniel F. Hoth, in "Present Status and Future Prospects for HIV Therapies," Science, Vol. 260, pages 1286–1293 (May 28, 1993), review some of the efforts of researchers to develop anti-HIV agents and report some of the well-accepted explanations as to why such agents have not been fully effective. One such explanation for drug failure is the emergence of drug resistance. Johnston and Hoth note that HIV resistance has been observed for each of the widely used antiretroviral nucleosides used to treat HIV. As an example, Johnston and Hoth refer to one such antiretroviral nucleoside, 3'-azidothymidine (AZT), which was identified in 1984 as being active against HIV in cell culture but which, today, has been observed to lead to resistance in individuals as quickly as 6 months after treatment has begun.

Another example of HIV drug resistance has recently emerged in connection with a new HIV protease inhibitor developed by Merck & Co. See M. Waldholz, "Merck faces dismay over test results: HIV resists promising new AIDS drug," *Wall Street Journal* (Feb. 25, 1994). No resistance to this drug, which Merck identifies under the trade designation L-735,524, had been observed in cell culture studies prior to human trials; however, during clinical evaluations, indications of resistance emerged.

Viral resistance to antiviral agents is typically conferred by one or more resistance-conferring mutations in the viral nucleic acid sequence encoding the targeted viral protein. Particularly in the case of certain retroviruses, such as the HIV virus, the mutational frequency can be quite high. In fact, in certain individuals infected with the HIV virus, as much as 20% of the viruses are found to contain mutations. See Wain-Hobson, "The fastest genome evolution ever described: HIV variation in situ," *Current Opinion in Genetics and Development*, 3:878–883 (1993). This high mutational frequency is primarily attributable to the operation of the HIV reverse transcriptase enzyme, which is used to convert single stranded viral RNA into double stranded DNA as part of the viral life cycle but which lacks an editing mechanism. Because of its high mutational frequency, the HIV virus has been characterized as "a perpetual mutation machine," id. at 881. In fact, there is a widespread belief in the art that, at least with respect to the HIV virus and similar viruses, a virtually unlimited number of distinct evolutionary escape pathways exist for any protein with respect to practically any drug. See e.g., Honess et al., "Single Mutations at Many Sites within the DNA Polymerase Locus of Herpes Simplex Viruses Can Confer Hypersensitivity to Aphidicolin and Resistance to Phosphonoacetic Acid," *J. gen. Virol.*, Vol. 65, pp. 1–17 (1984); Saag et al., "Extensive variation of human immunodeficiency virus type-1 in vivo," *Nature*, Vol. 334, pp. 440–444 (Aug. 4, 1988); Richman, "HIV Drug Resistance," *Annu. Rev. Pharmacol. Toxicol.*, Vol. 32, pp. 149–164 (1993); and Wain-Hobson, "The fastest genome evolution ever described: HIV variation in situ," *Current Opinion in Genetics and Development*, 3:878–883 (1993). Alternatively stated, there appears to be no recognition in the art that, at least with respect to certain drugs, the number of different resistance-conferring mutations available to a given protein may be quite limited. Consequently, HIV drug resistance (and, more broadly stated, viral drug resistance) is presently considered by the art to be an intractable problem.

One way in which prospective drugs have traditionally been evaluated prior to clinical use is by a technique commonly referred to as cell-culture selection. To test antiviral agents using cell-culture selection, one typically grows a targeted virus on a host cell line in the presence of a prospective drug. Progeny viruses are then serially passaged in the host cell line in the presence of an increasing concentration of the prospective drug to select drug-resistant strains. An exemplary application of cell-culture selection to prospective drug evaluation is disclosed in Tisdale et al., "Rapid in vitro selection of human immunodeficiency virus type 1 resistant to 3'-thiacytidine inhibitors due to a mutation in the YMDD region of reverse transcriptase," *Proc. Natl. Acad. Sci., U.S.A.*, Vol. 90, pp. 5653–5656 (June 1993). In Tisdale, MT-4 cells were infected with either wild-type HIV-1 or an AZT-resistant strain derived from wild-type HIV-1 and exposed to low concentrations of (−)-2'-deoxy-5-fluoro-3'-thiacytidine (FTC). Progeny virus was recovered and serially passaged in MT-4 cells in the presence of increasing FTC concentration. By the fourth passage of the wild-type progeny and only the second passage of the AZT-resistant progeny, $IC_{50}$ (50% inhibitory concentration) values exceeded 50 $\mu$M. When tested at higher compound concentrations, the $IC_{50}$ values of passage 6 virus were in excess of 250 $\mu$M. Based on the rapid emergence of resistant virus, Tisdale et al. postulated that the therapeutic value of FTC, except possibly in combination with other HIV-1 inhibitors, may be limited.

Another exemplary application of cell-culture selection to prospective drug evaluation is disclosed in Taddie et al., "Genetic Characterization of the Vaccinia Virus DNA Polymerase: Identification of Point Mutations Conferring Altered Drug Sensitivities and Reduced Fidelity," *Journal of Virology*, Vol. 65, No. 2, pp. 869–879 (February 1991). In Taddie, wild-type vaccinia virus was chemically mutagenized with nitrosoguanidine and then serially passaged through African green monkey BSC40 cells in the presence of 85 $\mu$M aphidicolin in an effort to isolate aphidicolin-resistant virus.

A technique analogous to the cell-culture selection technique described above for antiviral agents has been used to test the efficacy of antibiotics. See e.g., Handwerger et al., "Alterations in Penicillin-Binding Proteins of Clinical and Laboratory Isolates of Pathogenic *Streptococcus pneumoniae* with Low Levels of Penicillin Resistance," *The Journal of Infectious Diseases*, Vol. 153, No. 1, pp. 83–89 (January 1986) (wherein clones resistant to benzylpenicillin were selected by serial passage on blood agar plates in two-fold increasing concentrations of benzylpenicillin).

In testing both antibiotics and antiviral agents in the above manner, most investigators have focused primarily on the speed with which marked resistance to the prospective drug emerges and on the $IC_{50}$ values of the prospective drug as the key factors used to gauge the potential therapeutic value of the drug. Typically, the more rapid the development of resistance, the less desirable the prospective drug has been adjudged. Thus, in evaluating prospective drugs, the art focuses primarily on the rate of mutation, without regard to the nature or number of different drug-resistant mutants.

Although widely used, cell-culture selection is fraught with limitations. One such limitation is that the cell-culture technique itself may be unfairly biased against the selection of certain mutant strains that would have emerged in vivo. See Meyerhans et al., "Temporal Fluctuations in HIV Quasispecies In Vivo Are Not Reflected by Sequential HIV Isolations," *Cell*, Vol. 58, pp. 901–910 (Sep. 8, 1989). In the aforementioned Meyerhans article, HIV-1 isolates obtained from a patient over a two and one-half year period as well as from cultured peripheral blood mononuclear cells (PBMC) were analyzed and compared. The tat gene from the respective isolates was amplified by polymerase chain reaction (PCR), and amplified DNA was cloned into a mammalian expression vector. Twenty clones from each sample were sequenced. The HIV quasispecies—populations of viral genomes—showed significant differences between corresponding in vivo and in vitro samples. For example, the major form of one in vivo isolate was derived from the minor form of a corresponding in vitro isolate. From these results, Meyerhans et al. were led to conclude that "to culture is to disturb."

Another limitation inherent in cell-culture selection is that one is not assured that each and every mutation that may emerge in vivo will be generated for possible selection. Still another limitation inherent in cell-culture selection is that certain drug-conferring mutations may be masked by the simultaneous occurrence of lethal mutations in genes other than the gene under observation. This is because cell-culture selection affords no means for restricting mutagenesis to the gene under observation.

In UK Patent Application No. 2,276,621, published Oct. 5, 1994, and incorporated herein by reference, there is described a chromogenic assay said to be useful in the identification and isolation of drug-resistant HIV protease mutants. The assay is also said to be useful in the screening of new inhibitors of HIV protease, e.g., inhibitors not affected by drug-resistance of the HIV protease. The subject color screening assay contains a vector comprising a regulatable promoter which controls the transcription of two adjacent structural sequences, one sequence coding for HIV protease or a mutant thereof, the other sequence coding for beta-galactosidase with an amino acid substrate insert cleavable by HIV protease.

Unfortunately, as far as the present inventors are aware, the aforementioned chromogenic assay has had limited success in identifying, in vitro, drug-resistant strains that were later isolated following clinical use. The present inventors believe that the poor predictive nature of the aforementioned chromogenic assay is due, to a considerable extent, to the lack of authenticity in the HIV-protease/beta-galactosidase construct used therein. In other words, in the aformentioned chromogenic assay, the protease mutant need only cleave the protease/beta-galactosidase fusion protein at a single, artificial, cleavage site within the beta-galactosidase protein for a positive result to be registered in the assay; in contrast, in the native HIV polyprotein, the protease must cleave the polyprotein at a number of sites, e.g., at least three sites to activate HIV reverse transcriptase. The present inventors believe that these variations in the authenticity of the nature and number of cleavage sites in the construct of the above-described chromogenic assay effectively render the assay unreliable.

Consequently, for at least the above reasons, there are a number of reported instances in which drug-resistant strains have been observed in vivo which were not predicted by cell-culture studies. See e.g., Smith et al., "Resumption of Virus Production after Human Immunodeficiency Virus Infection of T Lymphocytes in the Presence of Azidothymidine," *Journal of Virology*, Vol. 61, No. 12, pp. 3769–3773 (December 1987) (reporting that no AZT resistance in the HIV virus was observed following cell-culture selection); Larder et al., "Infectious potential of human immunodeficiency virus type 1 reverse transcriptase mutants with altered inhibitor sensitivity," *Proc. Natl. Acad. Sci., U.S.A.,* Vol. 86, pp. 4803–4807 (July 1989) (reporting that no AZT resistance in the HIV virus was observed following cell-culture selection but noting the presence of AZT-resistant isolates following clinical use); and Larder et al., "Zidovudine-Resistant Human Immunodeficiency Virus Selected by Passage in Cell Culture," *Journal of Virology*, Vol. 65, No. 10, pp. 5232–5236 (October 1991) (noting that attempts to select zidovudine-resistant strains of HIV in cell culture using wild-type HIV have been unsuccessful and reporting that zidovudine-resistant strains similar to those found clinically were obtained by cell-culture selection of HIV variants constructed by site-directed mutagenesis).

Other limitations with cell-culture selection are that (1) stringent handling conditions must be used to avoid safety problems, since intact pathogens are required to be used; and (2) the cell-culture technique itself is very time consuming (and, hence, expensive) since several passages are usually required, each passage typically taking a number of days.

As alluded to above, because drug resistance is so common, many researchers have assumed that, in virtually every instance in which drug resistance occurs, there are a great many parallel evolutionary escape pathways by which drug resistance is or may be conferred. See Saag et al., "Extensive variation of human immunodeficiency virus type-1 in vivo," *Nature*, Vol. 334, pp. 440–444 (Aug. 4, 1988) (reporting that, following the sequential isolation of HIV virus from two chronically infected individuals, a remarkably large number of related but distinguishable genotypic variants had evolved in parallel); and Honess et al., "Single Mutations at Many Sites within the DNA Polymerase Locus of Herpes Simplex Viruses Can Confer Hypersensitivity to Aphidicolin and Resistance to Phosphonoacetic Acid," *J. gen. Virol.,* Vol. 65, pp. 1–17 (1984) (reporting that hypersensitivity of Herpes Simplex virus to aphidicolin is a common consequence of single, well-separated mutations).

In fact, the problem of drug resistance has grown to such a level that, with respect to pathogens like HIV, some researchers have concluded that future prospects for efficient therapy and prevention are bleak. See Wain-Hobson, "The fastest genome evolution ever described: HIV variation in situ," *Current Opinion in Genetics and Development,* Vol. 3, pp. 878–883 (1993) (explaining that the high genetic variability of the HIV virus and the high viral load of the HIV virus raise questions as to whether there are any limits to HIV variation).

Notwithstanding these pessimistic forecasts, new drugs and therapies are continuing to be explored. However, the identification of potential new drugs continues to involve evaluating possible therapeutic agents against a single, static, pathogenic target. Techniques increasingly being used to identify such potential new drugs include rational drug design and combinatorial screening. In rational drug design, the conformational and chemical structure of a desired binding site on a target compound is identified, and prospective drugs are designed and/or evaluated based on their ability to function as a binding partner for the binding site on the single target compound. Exemplary applications of rational drug design are discussed in the following patents and publications, all of which are incorporated herein by reference: U.S. Pat. No. 5,300,425; U.S. Pat. No. 5,223,408; and Roberts et al., "Rational Design of Peptide-Based HIV Proteinase Inhibitors," *Science,* Vol. 248, pp. 358–361 (Apr. 20, 1990).

In combinatorial screening, various combinatorial arrangements of short oligonucleotide sequences, amino acid sequences, or other organic compounds are screened as prospective binding partners for a binding site on a single target compound. Exemplary applications of combinatorial screening are discussed in the following patents and publications, all of which are incorporated herein by reference: U.S. Pat. No. 5,288,514; U.S. Pat. No. 5,258,289; Barbas, III et al., "Semisynthetic combinatorial antibody libraries: A chemical solution to the diversity problem," *Proc. Natl. Acad. Sci., USA,* Vol. 89, pp. 4457–4461 (May 1992); and Alper, "Drug Discovery on the Assembly Line," *Science,* Vol. 264, pp. 1399–1401 (Jun. 3, 1994).

Recently, the idea of co-administering two or more drugs directed at different proteins of a given pathogen, specifically HIV, ("combination therapy") has emerged as a possible way of overcoming the problem of drug resistance. Examples of approaches utilizing two or more drugs targeted against different proteins of a single pathogen are discussed in Kageyama et al., "In Vitro Inhibition of Human Immunodeficiency Virus (HIV) Type 1 Replication by $C_2$ Symmetry-Based HIV Protease Inhibitors as Single Agents or in Combinations," *Antimicrobial Agents and Chemotherapy*, Vol. 36, No. 5, pp. 926–933 (May 1992) and in "Pharmaceutical Consortium to Begin Clinical Trials of Combined AIDS Drugs," *Wall Street Journal* (Apr. 14, 1994). In the Kageyama article, for example, the effect of combinations of certain $C_2$ symmetry-based HIV protease inhibitors, such as A75925, A77003 and A76928, with AZT or ddI (reverse transcriptase inhibitors) was investigated in vitro. For certain combinations of drugs, encouraging in vitro results were observed. (For example, A75925 combined with AZT resulted in virtually complete suppression in vitro).

The present inventors believe, however, that combination therapy of the type described above will ultimately fail in vivo due to the emergence, under selective pressure, of pathogens containing resistant forms of all targeted proteins. The emergence of such pathogens may even be hastened in the event that genomes with resistance-conferring mutations in different targeted proteins recombine with one another to form multiply resistant pathogens.

Another approach that has recently emerged as a possible way of overcoming the problem of drug resistance is to co-administer two or more drugs directed at different active sites on the same protein of a given pathogen ("convergent combination therapy"). An example of this approach is disclosed in Chow et al., "Use of evolutionary limitations of HIV-1 multidrug resistance to optimize therapy," *Nature*, Vol. 361, pp. 650–654 (Feb. 18, 1993). In the Chow article, mutations in different active sites on the HIV-1 reverse transcriptase gene conferring multiple drug resistance to wild-type inhibitors of reverse transcriptase were constructed to determine whether multiple drug resistance is incompatible with viral replication. Viruses containing combinations of mutations conferring resistance to AZT, ddI and a pyridinone were reported to be incapable of viral replication. Chow et al. postulated that the existence of these mutant viruses indicated that evolutionary limits exist to restrict the development of multiple drug resistance. However, it was later pointed out in Chow et al., "HIV-1 error revealed," *Nature*, Vol. 364, page 679 (Aug. 19, 1993) that the multiply-drug-resistant mutant referred to above had unintended mutations which were responsible for its lack of viability. It was further pointed out in Emini et al., "HIV and multidrug resistance," *Nature*, Vol. 364, page 679 (Aug. 19, 1993) that the multiply-drug-resistant Chow mutant exhibited growth kinetics in the presence of inhibitors similar to wild-type virus while still exhibiting a multiply resistant phenotype.

The present inventors believe that convergent combination therapy of the type described above is flawed because each and every drug used therein is targeted against different sites on the same static species of the protein, namely the original or wild-type species. In other words, none of the drugs of the aforementioned convergent combination therapy are specifically directed against mutant, drug-resistant forms of the protein that may emerge under selective pressure, nor are any of the drugs of the aforementioned convergent combination therapy specifically directed against mutations which confer resistance to any of the other drugs of the combination. As a result, there can be no assurance that every mutant form of the protein that is resistant to one of the drugs of the combination will be rendered inactive by any of the other drugs of the combination.

Thus, as can be seen, the techniques utilized in the prior art to screen and compare prospective drugs, as well as to design clinical therapies, have been either ineffectual or impractical.

Accordingly, there presently exists a need for effective therapies against pathogenic microorganisms to overcome the problem of drug resistance. In addition, there is a need to predict, prior to clinical administration of a prospective drug, all possible, first-generation, drug-resistant, biologically-active mutants which could emerge in response to the drug, to compare drugs in terms of the ease with which resistance develops against them, and to identify drugs effective against such drug-resistant mutants. Further, there is a need for an in vitro technique that can be used to predict drug-resistant, biologically-active mutants of a protein to a subject drug in a manner that it is more time-efficient and economical than conventional cell-culture selection techniques.

SUMMARY OF THE INVENTION

The present invention is premised on the discovery that, in many instances, there are only a very small number of distinct initial evolutionary pathways that a protein can take in order to escape sensitivity to an effective inhibitory drug targeted thereagainst. This notion, that only a very small number of distinct resistance-conferring mutations are initially available to a protein in response to the use of an effective inhibitory drug targeted thereagainst, is contrary to the present thinking in the field of antimicrobial therapy. The design of therapies in the prior art has, thus far, failed to distinguish between resistance-conferring mutations and other mutations which, in combination with resistance-conferring mutations, confer incrementally higher levels of drug resistance.

One application of the aforementioned discovery is to an in vitro method for predicting the identity of all distinct, first-generation, drug-resistant, biologically-active mutants of an original (or "wild-type") protein that can possibly emerge in vivo in response to a drug contemplated for use thereagainst. In accordance with the teachings of the present invention, this in vitro method comprises the steps of: producing a comprehensive library of first-generation mutants of the original protein, said library including each first-generation mutant differing from the original protein or a region thereof by at least one, and preferably no more than three, amino acid substitutions; isolating in vitro all biologically-active, first-generation mutants from the comprehensive library that are resistant to the drug in question; identifying each first-generation, biologically-active mutant so isolated; whereby each mutant so identified, for which another mutant so isolated having the same amino acid sequence is not also identified, represents a distinct, first-generation, drug-resistant, biologically-active mutant that may emerge in vivo in response to the drug. Five different embodiments of the above-described method will be described in detail below. According to one particularly preferred embodiment, there is disclosed an in vitro method for predicting the identity of distinct, first-generation, drug-resistant, biologically-active mutants of proteases of the type which are natively expressed as part of a polyprotein with a second protein that has a biological activity catalyzed by cleavage of the polyprotein by the protease. Where, for example, the protease is HIV protease, the in vitro method preferably comprises the steps of (a) preparing, in the presence of the drug, a comprehensive library of all first-generation mutants of the protease differing therefrom by at least one and preferably no more than three amino acid substitutions, each of the protease mutants being generated as part of a polyprotein with the HIV reverse transcriptase protein; (b) isolating, in vitro, first-generation, drug-resistant, biologically-active, mutant proteases from said library by assaying for biological activity of the reverse transcriptase protein catalyzed by cleavage of the polyprotein by the protease; and (c) identifying the distinct, first-generation, biologically-active, mutant proteases so isolated.

As can readily be appreciated, because the general method described above permits virtually every first-generation mutation which may occur in vivo to be evaluated for drug resistance and biological activity, the present invention overcomes at least some of the inherent limitations discussed above in connection with cell-culture selection. Moreover, the present invention can be practiced with a mere subset of the functional proteins of a pathogen, and therefore, avoids the safety problems associated with the use of intact pathogens. Other advantages of the present method over cell-culture selection and other techniques will be described below or will become apparent below in connection with the detailed description of the present method.

Following the identification of the limited universe of distinct, first-generation, drug-resistant, biologically-active mutants of the targeted protein using the above-described in vitro method of the present invention, known methods may be used to identify auxiliary drugs that are active against said mutants, and a "cocktail" of drugs including the initial drug and one or more auxiliary drugs (or, alternatively, a single drug used against both the original protein and its first-generation mutant forms) can be developed to block all of the initial evolutionary escape pathways before resistance has an opportunity to occur. Such a "cocktail" of drugs, as contemplated in accordance with the present invention, differs from the combination of drugs suggested by the above-described "convergent combination therapy" of Chow et al. in that the drugs of the present cocktail are directed against the original protein and its first-generation, drug-resistant, biologically-active mutants preferably by focusing on the resistance-conferring mutations of the original protein as a means for blocking all of the evolutionary pathways), whereas the drugs of the convergent combination therapy of Chow et al. are all directed against different sites within a single temporally-static target. Accordingly, the cocktail of drugs develop ed pursuant to the present invention is expected to be more effective than existing techniques in overcoming the problem of drug resistance.

Another application of the above-described discovery is to an in vitro method for predicting the ultimate efficacy of a drug targeted against a particular protein. The present inventors have discovered that the ultimate efficacy of a drug is inversely proportional to the number of distinct, first-generation, drug-resistant, biologically-active mutants that emerge in response to the use of the drug. Consequently, a drug which, when tested in vitro, permits a relatively smaller number of distinct, first-generation, drug-resistant, biologically-active mutants to emerge will turn out to have greater ultimate efficacy in vivo than a drug which, when tested in vitro, permits a relatively larger number of distinct, first-generation, drug-resistant, biologically-active mutants to emerge. The same techniques described herein which are used to determine the identity of all first-generation, drug-resistant, biologically-active mutants readily enable a determination of the number of distinct first-generation, drug-resistant, biologically-active mutants.

The present invention is also directed to a novel technique for predicting, in vitro, distinct, drug-resistant, biologically-active mutants of a protein that may emerge in vivo in response to a drug targeted thereagainst. In accordance with the teachings of the present invention, this technique comprises the steps of: providing a library of nucleotide sequences, said nucleotide sequences encoding mutant proteins that differ from the original protein by at least one amino acid substitution; expressing said library of nucleotide sequences by heterologous expression to provide a library of mutant proteins; isolating, in vitro, drug-resistant, biologically-active mutant proteins from said library of mutant proteins; and identifying the mutant proteins so isolated, whereby every mutant protein so identified for which another mutant so isolated having the same amino acid sequence is not also identified represents a distinct, drug-resistant, biologically-active mutant that may emerge in vivo in response to the drug.

For purposes of the present specification and claims, the expression "heterologous expression," when applied to the expression of a library of mutant nucleotide sequences, is defined to mean expression of the library of mutant nucleotide sequences in a locus other than the native locus of the corresponding wild-type or original nucleotide sequence. Heterologous expression may take place within the same or a different microorganism from which the wild-type or original nucleotide sequence is derived or may take place in an in vitro system.

Because the aforementioned technique utilizes a heterologous expression system to express the mutant nucleotide sequences, the subject technique has several advantages over conventional cell-culture selection techniques. One such advantage is that one can conduct a more rapid evaluation of larger numbers of variants than one could using cell-culture. Therefore, one may be able to identify certain mutants using the present technique that one would not practically be able to identify using cell-culture. Another advantage of the present technique over comparable cell-culture techniques is that, in the present technique, one has the ability to limit the locus of mutation to a specific gene and/or to define the type and/or number of mutations whereas these types of controls cannot effectively be exerted using cell-culture. As a result, one may be able to identify certain mutants using the present technique that may not be revealed by cell-culture due to some inherent bias in cell-culture against certain mutations.

The present invention is also directed to nucleotide sequences corresponding to those drug-resistant, biologically-active mutant proteins identified in the manner described above. Such sequences may be useful for diagnostic and other purposes.

According to another feature of the present invention, there is described a method of evaluating, in vitro, the efficacy of a drug against a biologically-active mutant or wild-type form of a first protein, the first protein being a protease that is natively expressed as part of a polyprotein with a second protein, the second protein having a biological activity which is catalyzed by cleavage of the polyprotein by the protease. According to the teachings of the present invention, said method comprises the steps of: (a) providing a mutant polyprotein, said mutant polyprotein including the second protein, a biologically-inactive mutant form of the protease, and one or more sites cleavable by the biologically-active or wild-type form of the protease in such a way as to activate the second protein; (b) adding the drug to the mutant polyprotein; (c) then, adding the biologically-active or wild-type form of the protease to the mutant polyprotein; and (d) then, assaying for the presence of biological activity for the second protein, whereby the presence of biological activity for the second protein indicates that the drug is not efficacious against the biologically-active mutant or wild-type form of the protease tested. Preferably, the protease is HIV protease, and the second protein is the reverse transcriptase protein expressed with HIV protease as part of the HIV polyprotein.

One application of the above-described method is in the screening of prospective drugs against biologically-active mutant forms of the protease obtained in a clinical setting. Such mutant proteases may be obtained, for example, from tissue or blood samples of infected patients, from clinical isolates of pathogen grown in cell culture, or from amplified protease-encoding RNA or DNA obtained from an infected patient and expressed in an in vitro translation system.

The present invention is further directed to a kit for evaluating, in vitro, the efficacy of a drug against a biologically-active mutant or wild-type form of a first protein, the first protein being a protease that is natively expressed as part of a polyprotein with a second protein, the second protein having a biological activity which is expressed after cleavage of the polyprotein by the protease. In accordance with the teachings of the present invention, said kit comprises (a) a mutant polyprotein, said mutant polyprotein including the second protein, a biologically-inactive mutant form of the protease, and one or more sites cleavable by the biologically-active or wild-type form of the protease in such a way as to activate the second protein; (b) a biologically-active mutant or wild-type form of the protease which, when combined with the mutant polyprotein in the absence of an effective drug thereagainst, cleaves the mutant polyprotein in such a way as to activate the second protein; and (c) means for detecting the presence of biological activity for the second protein. Preferably, the protease is HIV protease, and the second protein is the reverse transcriptase protein expressed with HIV protease as part of the HIV polyprotein. The above-described kit may further comprise a set of three test tubes, the first test tube containing the mutant polyprotein, the second test tube containing the active protease, and the third test tube containing said means for detecting the presence of biological activity for the second protein.

As can readily be appreciated, the above-described kit enables one to rapidly evaluate the efficacy of prospective drugs against the active protease, without requiring the use of intact pathogens and/or cell culturing.

Finally, the present invention is also directed to an assay for detecting the presence of a protease of the type that is natively expressed as part of a polyprotein with a second protein, the second protein having a biological activity which is catalyzed by cleavage of the polyprotein by the protease. In accordance with the teachings of the present invention, said assay comprises (a) a mutant polyprotein, said mutant polyprotein including a biologically-inactive mutant form of the protease, said second protein, and one or more sites cleavable by an active form of the protease in such a way as to activate the second protein; and (b) means for detecting the presence of biological activity for the second protein. Preferably, the protease is HIV protease, the polyprotein is HIV polyprotein, and the second protein is HIV reverse transcriptase.

Additional applications, uses, features, aspects and advantages of the present invention will be set forth in part in the description which follows, and in part will be obvious from the description or may be learned by practice of the invention. In the description, reference is made to the accompanying drawings which form a part thereof and in which are shown by way of illustration specific embodiments for practicing the invention. It is to be understood that other embodiments may be utilized and that structural changes may be made without departing from the scope of the invention.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference symbols represent like parts.

DETAILED DESCRIPTION OF PREFERRED EMBODIMENTS

Figure 1:
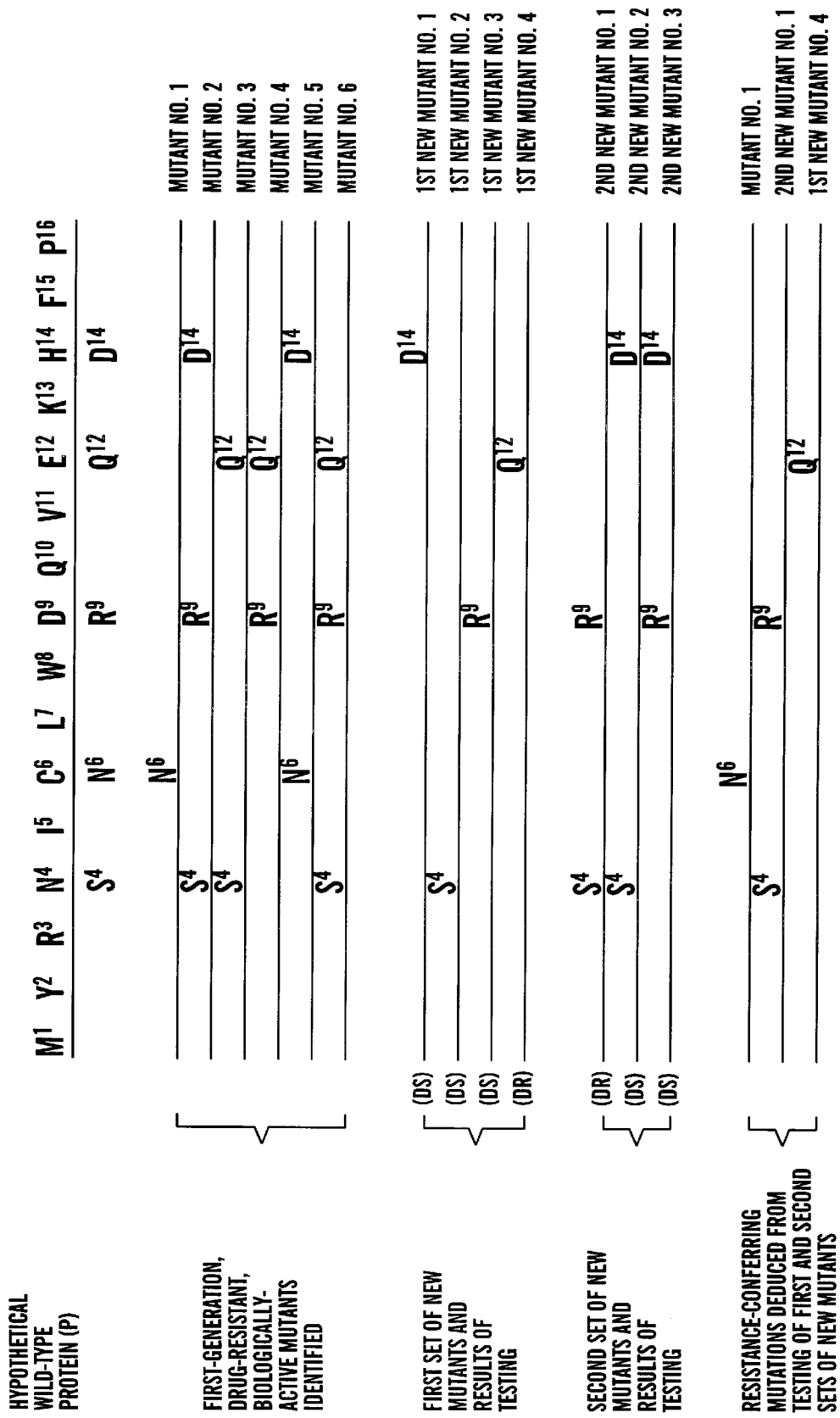
FIG. 1 is a schematic diagram of a method for identifying resistance-conferring mutations present in a set of first-generation, drug-resistant, biologically-active mutants.
Figure 2:
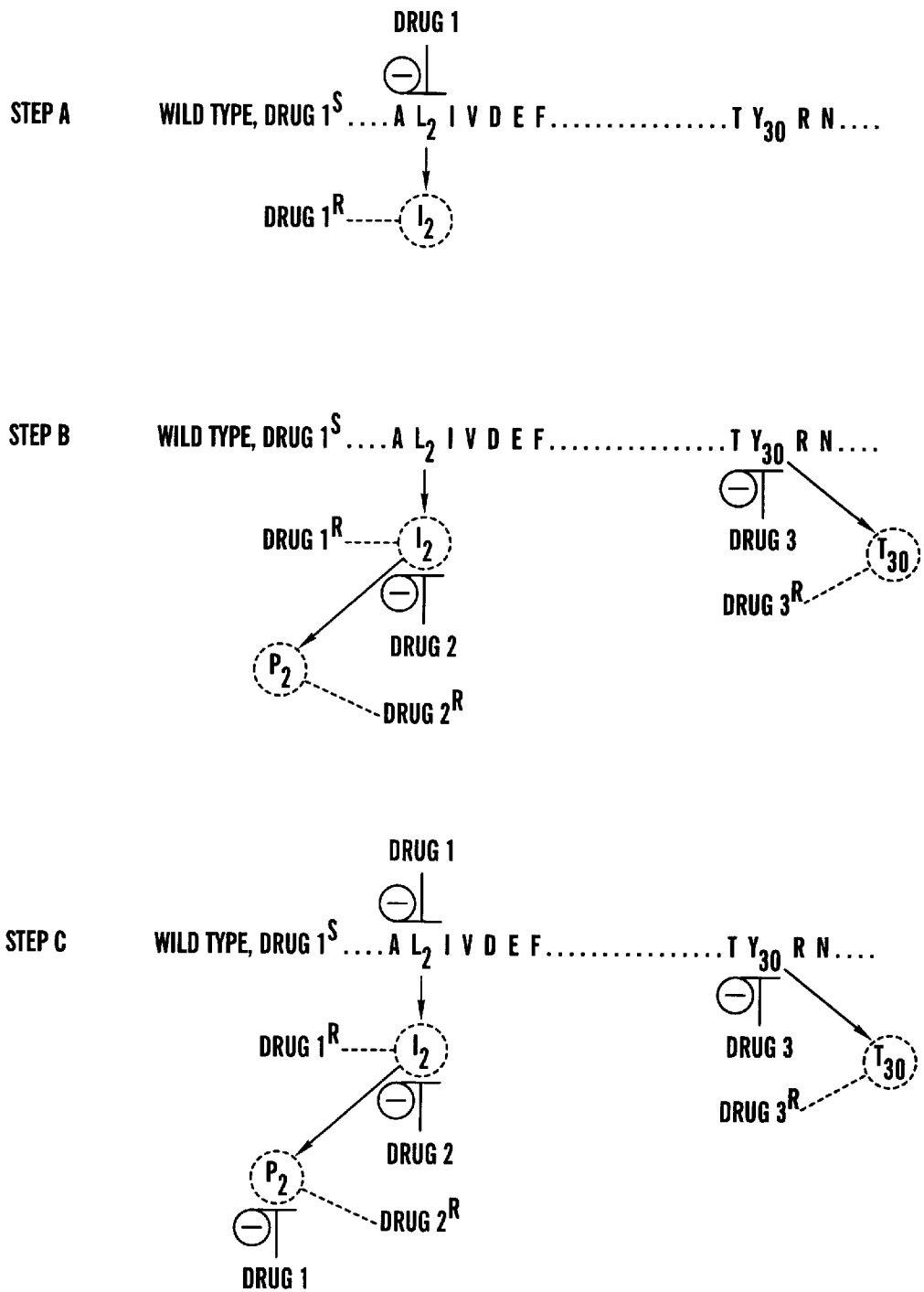
FIG. 2 is a schematic diagram of a method for identifying auxiliary drugs that act on a resistance-conferring mutation to an initial drug where 'R' denotes resistance to a drug and 'S' denotes drug susceptibility.

The present invention resulted from the inventors' empirical observations, leading to the discovery that, in many instances, there are only a very small number of distinct initial evolutionary escape pathways (i.e., resistance-conferring mutations) which are available to a protein to overcome sensitivity to an effective drug targeted thereagainst. Using this discovery, the present inventors have found that, by predicting in vitro the nature and number of all the distinct, first-generation, biologically-active mutants of a protein that may emerge in vivo in response to a particular drug targeted thereagainst, valuable information can be obtained which can be used to limit, or even prevent, resistance to said drug during clinical use.

For instance, the present inventors have discovered that, by identifying in vitro the nature of all distinct, first-generation, biologically-active mutants that are resistant to a particular drug, one or more auxiliary drugs that are active against said mutants can be identified (e.g., by existing techniques, such as rational drug design, combinatorial screening, or variations thereof), and a "cocktail" of drugs which includes the initial drug and the one or more auxiliary drugs thus identified (or, alternatively, a single drug used in place of both the initial drug and the one or more auxiliary drugs) can be developed to block all of the distinct initial evolutionary escape pathways of the original protein before resistance has an opportunity to occur during clinical use. Because the number of distinct, first-generation, biologically-active, drug-resistant mutants is limited, the total number of drugs required for an effective "cocktail" likewise should be limited.

Similarly, the present inventors have discovered that, by determining in vitro the number of all distinct, first-generation, biologically-active mutants that are resistant to a particular drug, one can predict the ultimate clinical efficacy of the drug. This is because the present inventors have discovered that the ultimate efficacy of a drug is inversely proportional to the number of distinct, first-generation, biologically-active mutants that are resistant to the drug. In this manner, if the number of such mutants is above some threshold value, the present invention enables one to predict the facile development of drug-resistant variants and, from this, to conclude that the drug is not a suitable drug to be used clinically. Appropriate threshold values for use in evaluating the ultimate efficacy of a drug as described above may be derived by observing the number of such mutants obtained under the same or similar conditions using drugs previously determined to possess high or low ultimate efficacy.

As can readily be appreciated, one could also use the principles set forth above to compare, prior to clinical use, two prospective drug candidates to see which will possess a greater ultimate efficacy, the more efficacious drug being the one which elicits a smaller number of distinct, first-generation, drug-resistant, biologically-active mutants.

It is important to differentiate between "long-term" efficacy (which was the concern of the prior art) and "ultimate" efficacy (which is the concern of the present invention). Indeed, when compared with the conclusions that could be drawn from prior art methods, the methods of the present invention could lead to vastly different conclusions about relative drug efficacies. Where, for example, a protein has only one first-generation, drug-resistant, biologically-active mutant which manifests itself rapidly in response to a given drug, the rapid development of drug resistance would lead one of ordinary skill in the art to conclude that the drug had limited long-term efficacy. On the other hand, if the same protein has four distinct, first-generation, drug-resistant, biologically-active mutants which manifest themselves slowly in response to a second drug, the delayed development of drug resistance would lead one of ordinary skill to conclude that the second drug had greater long-term efficacy. In contrast, one utilizing the teachings of the present invention would disregard the rate of mutation and focus instead on the number and nature of the mutants. By doing so, one would conclude that the first drug has greater ultimate efficacy, in that it need be combined with only one other therapeutic agent, i.e., an agent with therapeutic efficacy against the lone first-generation, drug-resistant, biologically-active mutant. (In all likelihood, the second drug would need to be combined with more than one additional therapeutic agent to combat the four distinct, first-generation, drug-resistant, biologically-active mutants.)

As utilized herein, the term "drug-resistant" refers to mutant proteins which maintain significant levels of activity or function in the presence of concentrations of a drug sufficient to inactivate or inhibit the function of wild-type protein. Such inhibitory concentrations are well-known for many drugs and, for other drugs, are readily ascertainable by routine procedures available to those of ordinary skill in the art.

In accordance with the teachings of the present invention, the manner in which the nature and/or number of distinct, first-generation, drug-resistant, biologically-active mutants of a targeted protein are determined is as follows: First, a comprehensive library of first-generation mutant forms of the protein is created, said library ideally including each first-generation mutant differing from the wild-type protein by at least one, and as many as four or more (but preferably no more than three), amino acid substitutions. Generally, such first-generation mutants are created by isolating the DNA sequence encoding the targeted protein, introducing specific point mutations into the DNA sequence encoding the targeted protein, and then expressing the protein using heterologous expression. Next, all biologically-active, first-generation mutants from the comprehensive library that are resistant to the drug in question are isolated in vitro. The amino acid sequence of each first-generation, drug-resistant, biologically-active mutant so isolated is then identified, for example, by sequencing the DNA fragment encoding the protein (see Sanger et al., "DNA sequencing with chain-terminating inhibitors," *Proc. Natl. Acad. Sci., USA,* Vol. 74, pp. 5463–5467, 1977, which is incorporated herein by reference) and deducing the corresponding amino acid sequence therefrom. By noting each first-generation, drug-resistant, biologically-active mutant so identified for which another first-generation, drug-resistant, biologically-active mutant having the same amino acid sequence is not also identified, one can deduce all of the distinct, first-generation, drug-resistant, biologically-active mutants that may emerge in vivo in response to the drug.

Preferably, the comprehensive library of first-generation mutants includes each mutant differing from the targeted protein by up to three amino acid substitutions of the original protein. Mutants having more amino acid substitutions may also be included in the library; however, the advantages of so expanding the library have to be weighed on a case-by-case basis against the additional time and cost of creating, using and analyzing the results from a library of such an expanded size. Some factors that may impact on the decision to expand the library to four or more amino acid substitutions include the size of the protein (the smaller the protein, the smaller the burden in increasing the library to include multiple amino acid substitutions); the manner in which the library of mutant forms of the protein is produced (e.g., whether the library is made using a "defined library" or a "randomized library" of DNA sequences, these two types of libraries and the differences therebetween being discussed below); whether a screening technique or a positive selection technique will be used as the in vitro identification technique for drug-resistant, screening techniques for testing large numbers of mutants); the variability of the protein in vivo (proteins of the HIV virus, for example, having a higher mutational frequency than many other microorganisms due to its lack of an editing mechanism); and the number of copies of pathogen typically found in an infected individual (i.e., the "pathogen load").

The nature and number of first-generation mutants of the wild-type protein that will be produced in vivo depend upon properties of the pathogen, such as the pathogen load and mutation rate of the pathogen. Consequently, in the vast majority of instances, there will be no reason to expand the library to include mutants having more than three amino acid substitutions since the probability of three or more simultaneous point mutations occurring in an infected individual is very low. To illustrate, in bacteria or viruses, a substitution mutation at a particular base pair can occur, per generation, at a range of frequencies from lower than $10^{-10}$ to, in the extreme case of HIV, as high as $10^{-4}$. Even for the extremely high estimated mutation frequency of HIV, three specific simultaneous base substitution mutations can occur only at a frequency of $10^{-12}$. By comparison, the number of pathogens present in an infected individual will be much smaller than the number of pathogens required by the above probabilities to assure the existence of mutants having three or more amino acid substitutions. For example, the proviral load of cells infected with the HIV virus has been estimated by one investigator to be $10^8$ to $5 \times 10^{10}$. See Wain-Hobson, "The fastest genome evolution ever described: HIV variation in situ," *Current Opinion in Genetics and Development*, Vol. 3, pp. 878–883 (1993). For many pathogens other than HIV, the number of copies of the pathogen present in an infected individual is considerably lower. Accordingly, based upon the frequency of mutation and the number of pathogens typically in an infected individual, it will typically be necessary for the library of mutants to only include up to three amino acid substitutions.

For purposes of the present specification and claims, the comprehensive library of mutants of the present invention may be confined to a comprehensive subset of those first-generation mutants of the original protein that differ from the original protein by at least one amino acid substitution. Such a comprehensive subset could include, for example, all first-generation mutants differing from the original protein by at least one amino acid substitution, wherein the at least one amino acid substitution is limited to a specific functional region of the protein, such as the catalytic pocket. Mutational libraries akin to the comprehensive subsets described above have previously been used, for example, to determine the relationship between the structure and function of various proteins. An example of the use of mutational libraries to gain insight into the relationship between structure and function of the HIV protease is described by Loeb et al. in "Complete mutagenesis of the HIV-1 protease," *Nature*, 340:397–400 (1989), which is incorporated herein by reference. However, the use of mutational libraries to find drug-resistance-conferring mutations and/or to discover drugs based upon prospective knowledge of drug-resistant mutants has not previously been described. Thus, unlike the comprehensive libraries of the preferred embodiment of the present invention, the mutational libraries of the prior art have only been used for purposes which do not require a comprehensive collection of every mutant differing from the original protein by at least one amino acid substitution, whether confined to a localized region of the protein or not.

It will be further appreciated that the comprehensive libraries contemplated in the present invention need not encompass substitution by every one of the 20 potentially available amino acids at a given location in the protein. In some instances, it will be desirable to deliberately omit certain amino acids from certain locations in the mutant proteins in the library, in order to maintain secondary structures or to introduce conformational constraints in the protein molecules. Thus, as used herein, a library containing "each" or "every" protein (that differs from the original protein or a region thereof by at least one amino acid substitution) is defined as a library that is comprehensive with respect to substitutions by each of the remaining amino acids, i.e., those not deliberately omitted.

As alluded to above, various techniques exist for synthesizing the above-described comprehensive libraries of first-generation mutants of a desired original protein. One such technique involves the expression of a library of isolated DNA sequences referred to, for purposes of the present specification and claims, as a "defined library." Another such technique involves the expression of a library of DNA sequences referred to, for purposes of the present specification and claims, as a "randomized library." Both defined and randomized libraries are synthesized by generating a series of DNA primers, each primer corresponding to a portion of the gene encoding the wild-type protein and differing from said gene portion by one or more base substitutions, and then applying the well-known technique of primer extension mismatch to synthesize the remainder of the gene using the primer without introducing any additional mutations thereinto. The manner in which said series of primers is made, however, differs depending upon whether the primers are to be used to make a defined library or a randomized library.

In the case of a defined library, the primers are made by synthesizing, using a DNA synthesizer, a defined DNA sequence that is identical to the corresponding DNA sequence for a portion of the wild-type protein at each base thereof, except at the bases of a single variant codon (or multiple variant codons). At the three constituent bases of said single variant codon (or multiple variant codons), equimolar amounts of all four possible bases (i.e., A, C, G and T) are made available to the DNA synthesizer to generate all 64 permutations of the codon. In contrast, in the case of a randomized library, a mixture of all four possible bases (i.e., A, C, G and T) is made available to the DNA synthesizer at every base of the sequence being synthesized. This mixture consists predominately of the wild-type base, with small equimolar amounts of the three alternative bases being added thereto. The average number of mutations per primer can be controlled by the ratio of wild-type to variant bases. The result of this type of synthesis is the production of primers with variations randomly distributed throughout their lengths, with the number of mutations per primer corresponding to a Gaussian distribution.

As can be appreciated, one advantage to using a "defined library" as opposed to a "randomized library" is that the type and number of mutations per primer can more closely be controlled in the former. Also, because of the Gaussian distribution of mutations in a randomized library, there will frequently be many sequences in such a library which have more than the desired number of mutations. Because, prior to the isolation and sequencing of their corresponding mutant proteins, those sequences having an excessive number of mutations cannot readily be distinguished from those sequences having a desired number of mutations, one is left with no option but to express all of the sequences in the "randomized library," then to isolate all of the corresponding drug-resistant mutants, then to sequence all of the isolated, drug-resistant mutants, and then to disregard those mutants having more than the desired number of mutations. Clearly, this approach may result in some unnecessary effort.

On the other hand, one advantage to using a randomized library over a defined library is that DNA sequences corresponding to mutants having multiple mutations can more easily and rapidly be generated.

As alluded to above, once all of the distinct, first-generation, biologically-active mutants of a wild-type protein that are resistant to an initial drug have been identified in the manner described above, one may wish to identify auxiliary drug(s) that are effective against all of said mutants so that the auxiliary drug(s), thus identified, can be used with the initial drug (or by itself, in the event that an auxiliary drug, thus identified, is effective against both the wild-type and all possible mutant forms of the protein) to block all of the distinct initial evolutionary escape pathways of the original protein before resistance has an opportunity to occur during clinical use.

One way in which to identify such auxiliary drug(s) is simply to test potential auxiliary drug(s) against all of the first-generation, drug-resistant, biologically-active mutants already identified, using the same type of procedure used to isolate the first-generation, drug-resistant, biologically-active mutants. Potential auxiliary drugs suitable for screening against the first-generation, drug-resistant, biologically-active mutants may be generated by existing techniques, such as by combinatorial chemistry. See Alper, "Drug Discovery on the Assembly Line," *Science*, Vol. 264, pp. 1399–1401 (Jun. 3, 1994), which is incorporated herein by reference. Those drugs which, either alone or in combination with one or more other drugs, are determined to be effective against all of the first-generation, drug-resistant, biologically-active mutants, qualify as auxiliary drugs likely to prevent drug-resistance.

An alternative method for identifying such auxiliary drug(s) involves first analyzing all of the distinct, first-generation, drug-resistant, biologically-active mutants to determine the identities of all of the "resistance-conferring mutations." For purposes of the present specification and claims, the expression "resistance-conferring mutations," when used in connection with a protein, refers to either a single amino acid substitution or a combination of amino acid substitutions which a protein must possess, at a minimum, in order to overcome sensitivity to a particular drug, without losing its biological activity. For purposes of the present specification and claims, a protein may have two or more "resistance-conferring mutations" which are capable of independently conferring resistance upon a protein. The expression "resistance-conferring mutation" is to be contrasted with the expression "neutral mutation" which, for purposes of the present specification and claims, when applied to a protein, refers to either a single amino acid substitution or a combination of amino acid substitutions which are not necessary to confer resistance to a particular drug on a protein (but which, in combination with a resistance-conferring mutation, may result in increased levels of resistance). As can readily be appreciated, a first-generation, drug-resistant, biologically-active mutant may include both one or more "resistance-conferring mutations" and one or more "neutral mutations."

The identities of the resistance-conferring mutations may be determined in the following manner: First, the amino acid sequence of each identified first-generation, drug-resistant, biologically-active mutant is compared to the amino acid sequence of the wild-type protein. Where the amino acid sequence of an identified first-generation mutant differs from the amino acid sequence of the wild-type protein by only a single amino acid substitution, that amino acid substitution represents a resistance-conferring mutation. Where, however, the amino acid sequence of an identified first-generation mutant differs from the amino acid sequence of the wild-type protein by two or more amino acid substitutions, each of said two or more amino acid substitutions is identified and a first set of new mutants of the wild-type protein is then created, each "new mutant" of said first set differing from the wild-type protein by a different one of the identified two or more amino acid substitutions. The aforementioned new mutants may be produced by expression of a mutant form of the gene encoding the protein, said mutant genes desirably being made using standard site-directed mutagenesis of the wild-type gene. See e.g., *Promega Protocols and Applications Guide,* Second Edition, 1991, pp. 98–122, Promega Corporation, Madison, Wis., which is incorporated herein by reference. Each new mutant is then tested for resistance against the drug in question. Each single amino acid substitution present in those new mutants identified as being drug-resistant then represents a resistance-conferring mutation.

Where the amino acid sequence of an identified first-generation mutant differs from the amino acid sequence of the wild-type protein by exactly two amino acid substitutions, and where one of those substitutions has been identified by the above-procedure as a resistance-conferring mutation, the other amino acid substitution usually represents a "neutral mutation" if the corresponding new mutant (containing the other single amino acid substitution) is identified as being drug-sensitive.

After following the foregoing procedure, if no resistance-conferring mutations have yet been identified for a mutant having two or more amino acid substitutions, or if a mutant has three or more amino acid substitutions and at least two of said substitutions, viewed individually, have not been determined to be resistance-conferring mutations, a second set of new mutants is produced and tested in the above manner, each "new mutant" of the second set differing from the wild-type protein by a different combination of two amino acid substitutions not previously identified individually as being "resistance-conferring mutations." In this manner, "combination" resistance-conferring mutations are identified. This process is then repeated, where applicable, for every successive integer combination of amino acid substitutions until all possible combinations of amino acid substitution have been tested.

An exemplary application of the above-described procedure for identifying resistance-conferring mutations from a set of first-generation, drug-resistant, biologically-active mutants is schematically depicted in FIG. 1, wherein six first-generation mutants (Mutant Nos. 1 through 6) emerging from a hypothetical wild-type protein (P) have been identified, the six mutants representing various combinations of five different amino acid substitutions ($N^4 \rightarrow S^4$; $C^6 \rightarrow N^6$; $D^9 \rightarrow R^9$; $E^{12} \rightarrow Q^{12}$; $H^{14} \rightarrow D^{14}$). Because a single amino acid substitution ($C^6 \rightarrow N^6$) conferred drug-resistance to Mutant No. 1, this substitution is immediately discernible as a resistance-conferring mutation. As can be seen, an initial step in identifying other resistance-conferring mutations is to produce a first set of new mutants (1st New Mutant Nos. 1 through 4) in which each of the aforementioned amino acid substitutions (except $C^6 \rightarrow N^6$) appears as the only amino acid substitution per molecule relative to the wild-type protein (P). Each of the new mutants is then tested for drug-resistance. In the present example, 1st New Mutant No. 4 is found to be drug-resistant (DR), whereas 1st New Mutant Nos. 1 through 3 are found to be drug-sensitive (DS). From this information, one can deduce that the $E^{12} \rightarrow Q^{12}$ amino acid substitution also constitutes an individual resistance-conferring mutation. However, $C^6 \rightarrow N^6$ and $E^{12} \rightarrow Q^{12}$ cannot be the only resistance-conferring mutations since Mutant No. 2 contains neither the $C^6 \rightarrow N^6$ nor the $E^{12} \rightarrow Q^{12}$ amino acid substitution. Therefore, one must next determine whether any combinations of amino acid substitutions constitute combination resistance-conferring mutations. This is accomplished by producing and testing a second set of new mutants (2nd New Mutant Nos. 1 through 3) in which various combinations of two amino acid substitutions not already found to be resistance-conferring (i.e., $N^4 \rightarrow S^4$; $D^9 \rightarrow R^9$; and $H^{14} \rightarrow D^{14}$) are introduced per molecule relative to the wild-type protein (P). In the present example, 2nd New Mutant No. 1 is found to be drug-resistant (DR) whereas 2nd New Mutant Nos. 2 and 3 are found to be drug-sensitive (DS). From this information, one can deduce that the $N^4 \rightarrow S^4$ and the $D^9 \rightarrow R^9$ amino acid substitutions together constitute a combination resistance-conferring mutation and that the $H^{14} \rightarrow D^{14}$ amino acid substitution is a neutral mutation.

Once the "resistance-conferring mutations" are identified in the above manner, prospective auxiliary drugs are then screened against each of those mutants differing from the wild-type protein solely by an individual or combination "resistance-conferring mutation" (e.g., Mutant No. 1, 2d New Mutant No. 1 and 1st New Mutant No. 4 of FIG. 1). Such prospective auxiliary drugs may be drugs which were previously tested for use as the initial drug, but which were determined to have less ultimate efficacy than the drug ultimately selected as the initial drug. Other prospective auxiliary drugs may be new drugs generated by combinatorial chemistry or other means. The manner in which said prospective auxiliary drugs are screened is as follows: First, the prospective auxiliary drugs are tested, one drug at a time, against each of the resistance-conferring mutants. If a single auxiliary drug is not found which is effective against all of the resistance-conferring mutants, combinations of two auxiliary drugs (then three auxiliary drugs, four auxiliary drugs, etc.) are tested against all of the resistance-conferring mutations. Once a single prospective auxiliary drug or a combination of prospective auxiliary drugs is found which is effective against all of the resistance-conferring mutants, the prospective auxiliary drug(s) is then tested, with and without the initial drug, against the entire library of first-generation mutants. (If a single prospective auxiliary drug has not previously been tested for use as an initial drug, it may be found, by itself, to have efficacy against the wild-type protein and the entire library of first-generation mutants.) If no drug-resistant, biologically-active mutants emerge, an effective therapy has been identified. If drug-resistant, biologically-active mutants do emerge, different combinations of the drugs are tested until no drug-resistant mutants from the entire library of first-generation mutants are identified. Drug-resistant mutants may emerge from the library at large that do not emerge from the group of resistance-conferring mutants, where a "neutral" mutation with respect to the initial drug acts a "resistance-conferring" mutation with respect to the auxiliary drug(s) being tested.

An alternative method of identifying suitable auxiliary drugs, a pathway-directed approach, is to screen prospective auxiliary drugs against each of the same mutants described above differing from the wild-type protein solely by an individual or combination "resistance-conferring mutation" (e.g., Mutant No. 1, 2d New Mutant No. 1 and 1st New Mutant No. 4 of FIG. 1) and then to identify those drugs which are effective against those mutants and which interact with the mutants at the sites of the resistance-conferring mutations. An exemplary application of the aforementioned technique is schematically depicted in FIG. 2 where, for simplicity, a single resistance-conferring mutation $L_2 = I_2$ is shown as emerging in response to the administration of a first drug, Drug 1, to a wild-type protein (see Step A of FIG. 2). After screening a multitude of prospective auxiliary drugs against the $I_2$ containing mutant, a pair of drugs, Drug 2 and Drug 3, are determined to be effective; however, the site of interaction between the $I_2$ containing mutant and each of Drugs 2 and 3 is unknown at this time. Therefore, to determine the respective sites of interaction, one generates a comprehensive library of $I_2$ mutants and screens each of the drugs previously determined to be effective against the $I_2$ containing mutant against the comprehensive library of mutants to the $I_2$ containing mutant. As seen in Step B of FIG. 2, if resistance to one of the drugs only arises as a result of a mutation to the resistance-conferring mutation, the site of interaction between the drug and the protein is at the site of the resistance-conferring mutation. If, however, resistance to one of the drugs arises as a result of a mutation elsewhere in the protein (as is the case with Drug 3), the site of interaction between the drug and the protein is at a site other than the site of the resistance-conferring mutation. As can be seen in Step C of FIG. 2, since it has previously been determined that the Drug 2-resistant mutant is susceptible to Drug 1, then the combination of Drug 1 and Drug 2 can be used to completely inhibit the mutational escape pathway of the protein, thereby blocking the development of drug resistance. By contrast, the combination of Drug 1 and Drug 3 may not block drug resistance since Drug 1 is not likely to be effective against a mutant containing both $I_2$ and $T_{30}$ mutations.

Set forth below are five examples of in vitro techniques which may be used to predict the nature and number of all the distinct, first-generation, drug-resistant, biologically-active mutants that may emerge in vivo in response to a particular drug. The first technique is adapted for use in evaluating the evolutionary response of virtually any type of protein. The other four techniques are more specifically adapted for use in evaluating the evolutionary response of a protein, such as HIV protease, which has autocatalytic activity and which is expressed as part of a polyprotein. To illustrate the methodology of these five techniques, the HIV-1 protease protein, which is expressed in vivo by the HIV virus as part of a polyprotein, is used as the protein for all five techniques. HIV-1 protease is a comparatively small protein (homologous dimers of 99 amino acids), is required for viral maturation and infectivity, and hydrolyzes the gag-pol polyprotein in an ordered fashion. The enzyme has been expressed in active form in several expression systems, and sensitive in vitro assays have been developed.

EXAMPLE 1

(The technique of the present example includes a labor-intensive screening step and is, therefore, better suited for those situations in which the number of first-generation mutant protein molecules is relatively small, i.e., where there is an average of up to two amino acid substitutions per protein molecule.)

A DNA synthesizer is used both to synthesize the entire HIV-1 protease gene, 297 bp, and to incorporate an average of three random amino acid substitutions into each corresponding variant protein molecule. Preferably, the gene is synthesized as four distinct 80-base-pair partially overlapping DNA single strands whose 5' and 3' ends allow ligation into an appropriate expression vector.

The overlapping 80-base-pair segments are then converted into one double stranded DNA segment using the Klenow fragment of E. coli polymerase 1. The double stranded segments are then ligated into appropriate expression vectors and are transformed into appropriate expression hosts. A variety of appropriate bacterial and yeast expression vectors and hosts are currently available and suitable for the expression of HIV-1 protease. These include S. cerevisiae (both secretion and internal production) and E. coli (both as insoluble and soluble internal proteins as well as periplasmic localization). Other expression systems include Pichia pastoris or E. coli containing the gene for bacterial release protein that increases cell porosity. The key requirement for an appropriate expression system is that it permit expression of active protein in a sufficient quantity to be assayed. Because of the potential for bias in any expression system, it may be desirable to use two different and complementary (e.g., secretion and internal production) expression systems.

The transformed expression hosts are then grown, and the isolates are screened for drug-resistant HIV-protease activity. This is done by using a single isolate to inoculate a microtitre well containing a calorimetric assay for HIV-1 protease activity and an HIV-1 protease inhibitor, such as L-735,524 or A77003 (see Ho et al., "Characterization of Human Immunodeficiency Virus Type 1 Variants with Increased Resistance to a $C_2$-Symmetric Protease Inhibitor," Journal of Virology, Vol. 68, No. 3, pp. 2016–2020 (March 1994) and Kageyama et al., "In Vitro Inhibition of Human Immunodeficiency Virus (HIV) Type 1 Replication by $C_2$ Symmetry-Based HIV Protease Inhibitors as Single Agents or in Combinations," Antimicrobial Agents and Chemotherapy, Vol.36, No.5, pp.926–933 (May 1992), both of which are incorporated herein by reference). A variety of HIV-1 protease activity assays are currently available (see e.g., Richards et al., "Sensitive, Soluble Chromogenic Substrates for HIV-1 Proteinase," J. Biol. Chem., 265: 7733–7736 (1990); and Nashed et al., "Continuous Spectrophotometric Assays for Retroviral Proteases of HIV-1 and AMV," BBRC, 163: 1079–1085 (1989), both of which are incorporated herein by reference).

Any isolates which show protease activity in the presence of the inhibitor are identified and analyzed by DNA sequence analysis, and the identities of the distinct first-generation, drug-resistant, biologically-active mutant forms of the original protein substrate are deduced therefrom.

EXAMPLE 2

The technique of the present example makes use of the fact that the HIV-1 protease protein and the HIV-1 reverse transcriptase protein are initially expressed by the HIV-1 virus as part of the HIV-1 polyprotein. Cleavage of the HIV-1 polyprotein to produce the individual protease and reverse transcriptase proteins results from the autocatalytic activity of the protease protein on specific cleavage sites within the polyprotein.

Polymerase chain reaction (PCR), using low error incorporating Vent polymerase, is used to amplify the DNA sequence encoding HIV-1 polyprotein from the vector pART-2 (NIH AIDS Research and Reference Reagent Program). The primers used for the PCR amplification are designed to contain restriction sites to allow the subcloning of the amplified HIV-1 polyprotein into a fusion protein vector and to allow the subcloning of the entire fusion construct into different expression vectors. DNA sequence analysis is used to confirm that the PCR-amplified DNA is free of errors.

The amplified HIV-1 polyprotein DNA is then inserted into a fusion protein vector for E. coli maltose binding protein (New England Biolabs) to enable expression of the polyprotein as part of a maltose fusion protein. As will be seen below, the maltose binding protein is later used as an affinity ligand for binding the fusion protein to specific resins. Other proteins to which the HIV-polyprotein may be suitably fused and which can similarly serve as affinity ligand are, for example, the FLAG antigen (IBI) and the "Pinpoint" Biotin tagged fusion protein (Promega Inc.). For reasons that will become apparent below, the fusion protein must not undergo spontaneous cleavage except under the influence of its own active constituent protease. Furthermore, the protease must be active within the fusion protein construct.

Figure 3:
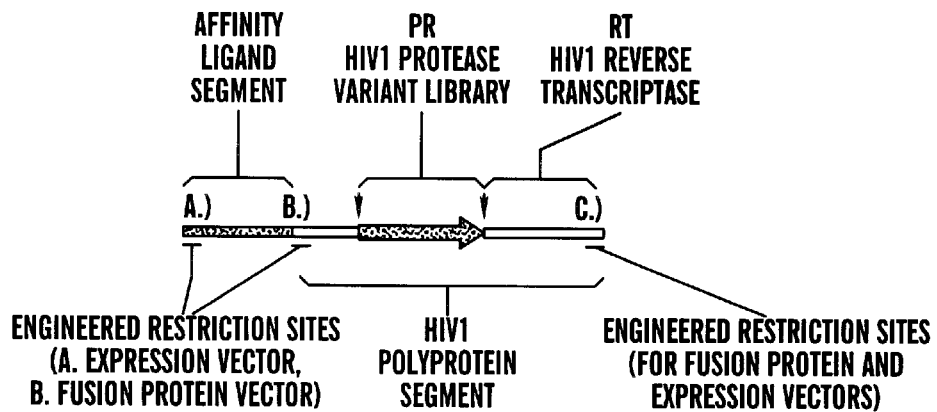
FIG. 3 is a schematic diagram of a DNA sequence encoding a fusion protein of the type used in the technique of Example 2 of the present invention.
Figure 4:
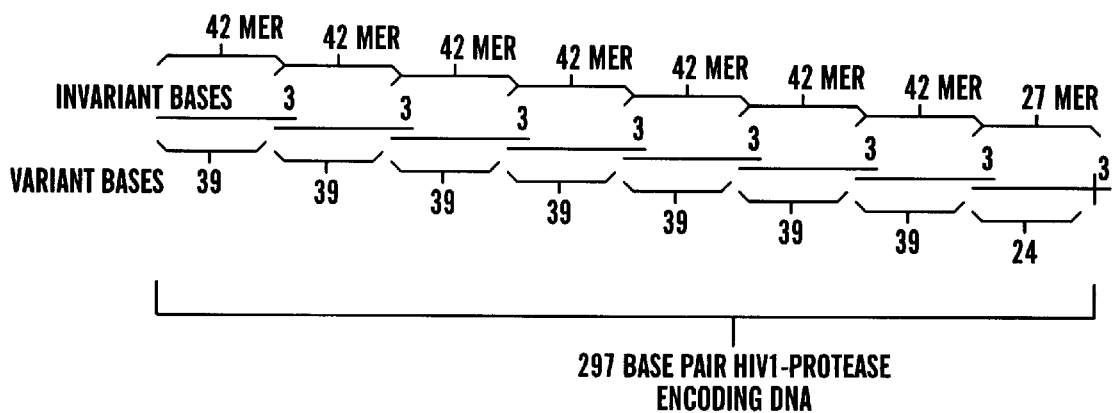
FIG. 4 is a schematic diagram of the seven 42-mers and one 27-mer used in the technique of Example 2 of the present invention.

The fusion protein construct (see FIG. 3) is then inserted into the phagemid vector pALTER (Promega Inc.) for use in producing pALTER/fusion proteins, and mutagenesis is performed by the well-known primer extension mismatch method using the following series of "defined library" primers: A series of 6,336 different HIV-1 protease gene primers, consisting of 5824 different 42-mers and 512 different 27-mers and cumulatively spanning the length of the 297 base pairs of the HIV-1 protease gene (as well as the next three base pairs of the remainder of the polyprotein), are synthesized by a DNA synthesizer. As can be seen in FIG. 4, the 5824 different 42-mers and the 512 different 27-mers correspond to seven sets of 832 different 42-mers and one set of 512 different 27-mers, respectively. Each of the seven sets of 42-mers is generated by synthesizing a set of DNA sequences identical to the corresponding wild-type 42-mer, except that all 64 nucleotide permutations are introduced into one codon per molecule for all of the codons except for the codon at the 3' end. The one set of 27-mers is similarly generated by synthesizing a set of sequences identical to the corresponding wild-type 27-mer, except that all 64 nucleotide permutations are introduced into one codon per molecule for all of the codons except for the codon at the 3' end. The 64 nucleotide permutations are generated by using equimolar amounts of A,G,C,T bases at the three positions of the randomized codon. The codons at the 3' ends of the respective 42-mers and 27-mers are kept constant so as to lower the possibility of poor primer extension.

Following the use of the above-described series of primers in the primer extension mismatch method, a library of 6,336 different mutant pALTER/fusion protein vectors is produced, each mutant vector being identical to the original pALTER/fusion protein vector described above, except for the substitution of between one to three base pairs in a single codon of the protease coding sequence.

(As can readily be appreciated, the library of mutant pALTER/fusion protein vectors could additionally include every mutant protease gene differing from the wild-type gene by between one to three base pairs in two or three codons of the protease coding sequence. However, the generation of such mutants using "defined library" primers having mutations in two or three codons would likely be labor-intensive.)

The library of mutant pALTER/fusion protein vectors described above is then amplified by transforming bacteria with the vectors and allowing the bacteria to grow. Following amplification, the fusion protein constructs are excised from their respective pALTER/fusion protein vectors and are inserted into expression vectors. Alternatively, pALTER may be also be used as the expression vector. Bacteria are then transformed with the expression vectors, preferably at a rate of only one vector per bacterium. The bacteria are then grown, and thereafter, the bacteria are distributed into the wells of a 96-well microplate having a well capacity of approximately 1 ml (Zymark, Inc.). Preferably, only a few cells (more preferably only one cell) are distributed into each well. The optical density of the stock culture can be used to estimate cell concentration, and the culture may be diluted so that the desired number of cells can be distributed to each well.

Figure 5:
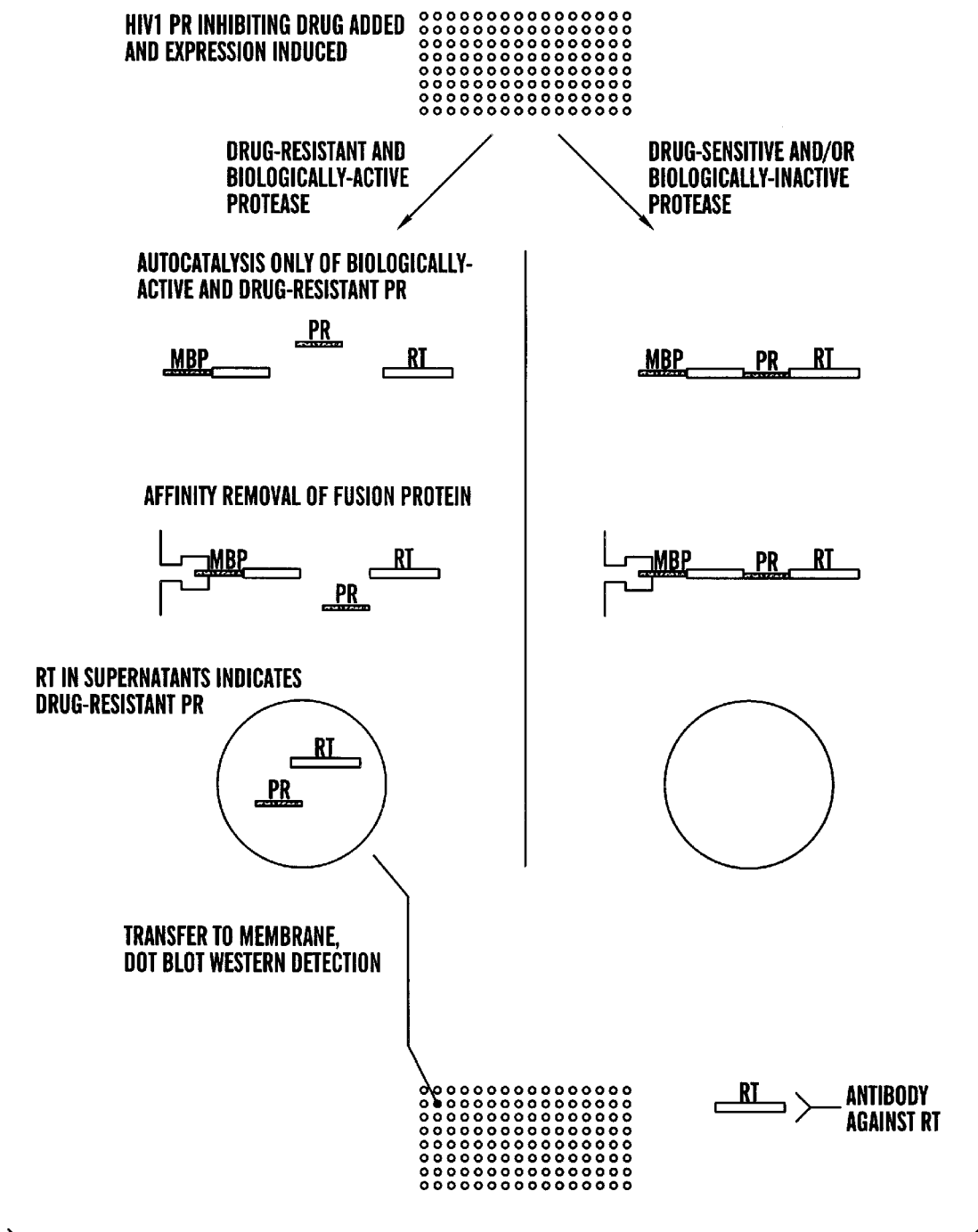
FIG. 5 is a schematic diagram of the procedure detailed in the technique of Example 2 of the present invention for isolating, in vitro, those first-generation mutants that are biologically-active and resistant to the drug in question.

Referring now to FIG. 5, there is shown schematically a procedure for isolating those first-generation mutant forms of the HIV-1 protease protein that are biologically-active and resistant to the drug in question. As can be seen, after the cells have been distributed into their respective wells, the protease inhibitory drug is added thereto and expression of the fusion protein is induced. In those instances in which the fusion protein contains a mutant form of the protease which is biologically-active and resistant to the protease inhibitor, the fusion protein is cut by the mutant protease into three separate proteins corresponding to the maltose binding protein (MBP), the mutant protease (PR) and the reverse transcriptase protein (RT). By contrast, in those instances in which the fusion protein contains a mutant form of the protease which is biologically-inactive and/or is sensitive to the protease inhibitor, the fusion protein remains as one long polypeptide comprising the maltose binding protein, the mutant protease and the reverse transcriptase protein.

Following expression of the fusion protein by the bacterial cells, the protein is released from the bacterial cells into the wells by a well-known extraction technique, such as by using freeze/thaw cycles, by applying lysozyme to the cells, by using cold osmotic shock for periplasmically exported protein constructs, or by using cells which can inducibly produce bacteriocin release protein (BRP). This last possibility is preferred because bacterial cells co-transformed with the fusion protein expression plasmid and a plasmid expressing BRP can be induced to permeabilize their outer membranes, resulting in release of the expressed fusion protein.

Next, amylose resin or another resin having an affinity for maltose binding protein (where affinity ligands other than maltose binding protein are used, the selected resin will have an affinity therefor) is added to each of the wells, and the wells are centrifuged to sediment the resin. Because the maltose binding protein complexes with the amylose resin, those intact fusion proteins comprising a biologically-inactive and/or drug-sensitive protease mutant are sedimented with the resin whereas, in the case of those fusion proteins which contain a biologically-active, drug-resistant protease mutant, only the maltose binding protein portion thereof is sedimented with the resin, the biologically-active, drug-resistant protease mutant and the reverse transcriptase proteins remaining in the supernatant. The supernatant from each of the wells is then transferred to a nitrocellulose membrane using a 96 tip multiple pipetter (Zymark, Inc.) and a Bio-Rad 96 well "Bio-Dot" microfiltration unit. Standard immunological techniques are then used to detect reverse transcriptase on the nitrocellulose membrane using polyclonal HIV-1 reverse transcriptase antibodies (NIH AIDS Research and Reference Reagent Program). Alternatively, the reverse transcriptase activity in the supernatant may be assayed directly. The presence of reverse transcriptase indicates a biologically-active, drug-resistant protease mutant.

For wells producing a positive signal, the cells corresponding thereto are re-plated to obtain single colonies, each of which is then re-tested in the same manner described above for drug-resistant autocatalytic activity. Standard DNA sequence analysis is then performed on the entire 297 base length of each confirmed drug-resistant mutant to determine the distinct, first-generation, drug-resistant, biologically-active mutants.

EXAMPLE 3

The technique of the present example is a variation on the well-known phage display selection technique. See e.g., Matthews et al., "Substrate Phage: Selection of Protease Substrates by Monovalent Phage Display," *Science*, Vol. 260, pp. 1113–1117 (May 21, 1993); McCafferty et al., "Phage antibodies: filamentous phage displaying antibody variable domains," *Nature*, Vol. 348, pp. 552–554 (Dec. 6, 1990); and Amberg et al., "SurfZAP™ Vector*: Linking Phenotype to Genotype for Phagemid Display Libraries, *STRATEGIES in molecular biology*, Vol. 6, pp. 2–4, all of which are incorporated herein by reference.

In accordance with the present example, a "defined library" of DNA sequences encoding all single amino acid substitutions within the HIV-1 protease portion of the HIV-1 polyprotein are obtained in the manner described in Example No. 2. A "randomized library" of DNA sequences encoding an average of up to three randomly distributed amino acid substitutions within the protease portion of the HIV-1 polyprotein is also generated.

Figure 6:
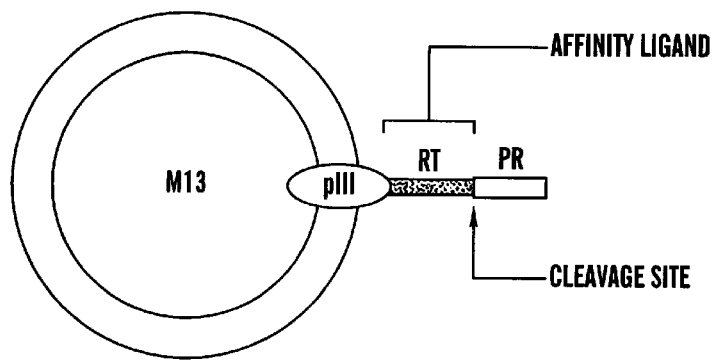
FIG. 6 is a schematic diagram of a phage particle produced using the technique of Example 3 of the present invention, the phage particle having a protein coat which contains a pIII/HIV-1 polyprotein fusion protein.
Figure 7:
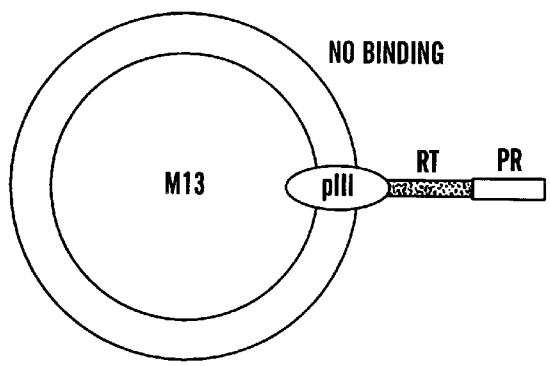
FIG. 7 is a schematic diagram of a phage particle of the type shown in FIG. 6, the phage particle having a protein coat which contains a biologically-inactive and/or drug-sensitive mutant form of the HIV-1 protease.
Figure 8:
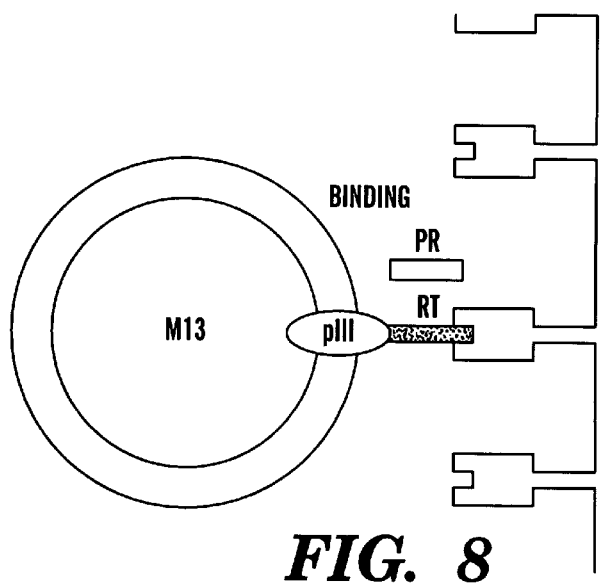
FIG. 8 is a schematic diagram of a phage particle of the type shown in FIG. 6, the phage particle having a protein coat which contains a biologically-active, drug-resistant mutant form of the HIV-1 protease.

The aforementioned DNA sequences are then inserted into the pIII encoding gene of the M13 phage so that, upon expression, pIII/HIV-1 polyprotein fusion proteins are produced. The recombinant M13 phage particles, thus constructed, are then used to infect *E. coli* cells. The *E. coli* cells are, in turn, induced to produce progeny phage particles in the presence of a protease inhibiting drug. Because pIII is a surface exposed antigen on the phage plasmid, the HIV-1 polyprotein fused thereto is also exposed as an accessible agent on the surface of the phage particle. As can be seen in FIG. 6, the pIII/HIV-1 polyprotein fusion protein contains, between the pIII protein and the protease, the HIV reverse transcriptase protein. Accordingly, if the protease mutant is biologically-active and drug-resistant, it cleaves itself from the remainder of the pIII/HIV-1 polyprotein, thereby exposing the reverse transcriptase protein for binding to a sequestered antibody or other agent with specific affinity for reverse transcriptase (see FIG. 8). If, however, the protease mutant is biologically-inactive and/or drug-sensitive, the pIII/HIV-1 polyprotein remains intact and the reverse transcriptase protein is not exposed for binding (see FIG. 7). In this manner, phage particles corresponding to the biologically-active, drug-resistant protease mutants can be selected based on their ability to bind to the binding agent.

(Several enrichments may be required to isolate a high percentage of biologically-active, drug-resistant mutants.) DNA from the selected phage particles is then sequenced to determine the nature of the drug-resistance conferring mutation.

In contrast with the screening techniques described in Example Nos. 1 and 2, the technique of the present example is a positive selection technique and, as such, permits the rapid selection of sought-after variants from a large library of variants (e.g., libraries containing about $10^{12}$ variants) without requiring that each and every variant be screened.

EXAMPLE 4

The technique of the present example is a variation on the well-known "two hybrid" interaction trap technique for selecting proteins based on their affinity for a given protein. See Fields et al., "A novel genetic system to detect protein-protein interactions," Nature, Vol. 340, pp. 245–246 (Jul. 20, 1989), which is incorporated herein by reference. The "two hybrid" technique makes use of the fact that the GAL4 transcriptional activator of the yeast Saccharomyces cerevisiae contains two spatially and functionally distinct domains, one that binds a specific DNA sequence and the other that activates transcription. The GAL4 transcriptional activator is only functional if the DNA binding and transcription activating domains, respectively, are somehow linked together, either covalently (for example, by an intact protein which interconnects the two domains) or by affinity (for example, where each domain is covalently bound to an affinity domain and where the two affinity domains have a high specific affinity for one another).

Figure 9:
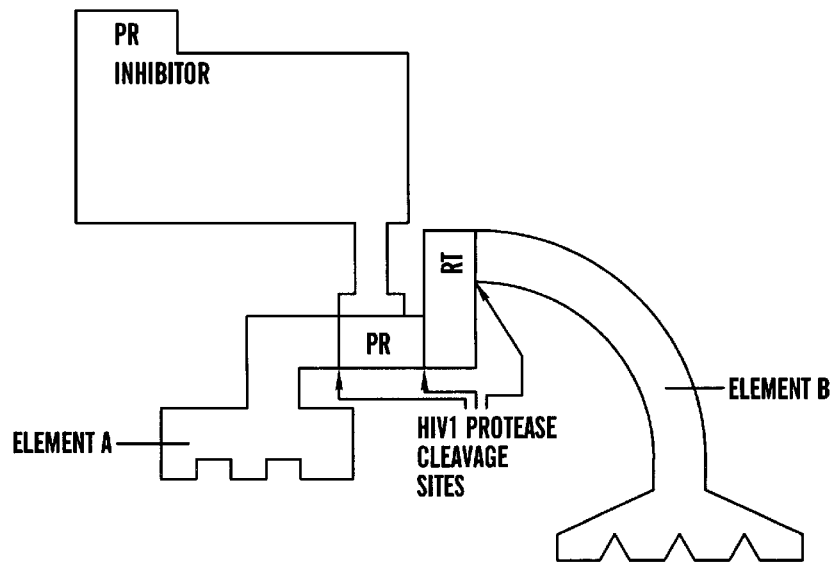
FIG. 9 is a schematic diagram of a GAL4 transcriptional activator/HIV-1 polyprotein fusion protein produced in accordance with the technique of Example 4 of the present invention, the HIV-1 polyprotein containing a drug-sensitive and/or biologically-inactive mutant form of the HIV-1 protease protein.

In accordance with the present technique, a "defined library" of DNA sequences encoding all single amino acid substitutions within the HIV-1 protease portion of the HIV-1 polyprotein and a "randomized library" of DNA sequences encoding an average of three randomly distributed amino acid substitutions per molecule within the protease portion of the HIV-1 polyprotein are prepared in the manner described above. These DNA sequences encoding the HIV-1 polyprotein are then inserted into a first S. cerevisiae expression vector containing the DNA sequence encoding the GAL4 transcriptional activator so that, upon expression, a GAL4 transcriptional activator/HIV-1 polyprotein fusion protein is produced in which the HIV-1 polyprotein is located between the DNA binding element (element a) and the transcriptional activator element (element b) of the GAL4 transcriptional activator. (See, e.g, FIG. 9.)

A strain of S. cerevisiae yeast is then engineered to contain deletion mutations of the GAL4 gene, the URA3 gene (the expression product of which is necessary for uracil biosynthesis) and the LYS2 gene (the expression product of which is necessary for lysine biosynthesis) at their native genomic loci. In addition, integrated transformation is used to place, in the yeast genome, copies of the URA3 and LYS2 genes which are constructed to be under the transcriptional control of the GAL1 promoter. A plasmid encoding the GAL4/HIV-1 polyprotein fusion protein described above is then taken up by the yeast strain.

Figure 10:
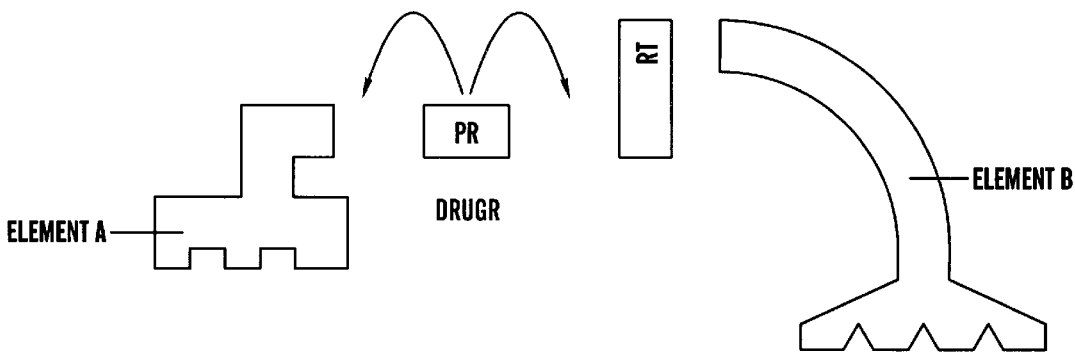
FIG. 10 is a schematic diagram of a GAL4 transcriptional activator/HIV-1 polyprotein fusion protein produced in accordance with the technique of Example 4 of the present invention, the HIV-1 polyprotein containing a drug-resistant, biologically-active, mutant form of the HIV-1 protease protein.

With the strain of S. cerevisiae thus engineered, expression of the URA3 and LYS2 genes requires that elements a and b of the GAL4 transcriptional activator be linked together by the intact HIV-1 polyprotein. In the presence of a protease inhibitory drug, linkage will occur where the protease mutant is drug-sensitive and/or biologically-inactive (see FIG. 9). Linkage will not occur in the presence of a protease inhibitory drug where the protease mutant is drug-resistant and biologically-active (see FIG. 10). As can be seen in the Table below, linkage can be selected by growing the strain in a medium lacking uracil and lysine, or a counterselection can be made by growing the strain in medium containing 5 fluoro-orotic acid (5-FOA) and alpha amino adipate (alpha AA). 5-FOA kills cells which express the URA3 gene, and alpha AA kills cells which express the LYS2 gene. Consequently, growth of this strain in medium containing alpha AA and 5-FOA (and supplemented with uracil and lysine) can only occur if the two complementary GAL4 fusion proteins do not bind to one another.

TABLE

| Mutant type | Selection Medium ura$^-$ lys$^-$ | Counterselection Medium 5-FOA, aAA |
|---|---|---|
| Drug-sensitive and/or biologically-inactive | + | – |
| Drug-resistant and biologically-active | – | + |

The above-described strain of yeast cells is grown in medium containing both the protease inhibitory drug and the gene-specific poisons 5-FOA and alpha AA. The cells with drug-sensitive or biologically-inactive protease mutants are killed due to GAL4 transcription of the URA3 and LYS2 genes. In contrast, the cells with drug-resistant mutants survive since the two complementary parts of the GAL4 activator, once cleaved by the HIV-1 protease protein, cannot be re-joined together.

Those cells which are selected by the above procedure are then analyzed by isolation and sequencing of the plasmid DNA containing the HIV-1 protease encoding gene.

The present technique is not limited to the selection of drug-resistant mutants of HIV-1 protease and can be used to select for drug-resistance in mutants of any viral protease which undergoes autocatalytic maturational cleavage to release itself from a larger protein, or any protease which can be expressed in recombinant form as an artificial fusion protein which contains protease substrate cleavage targets which are cleaved from the fusion protein by its active protease component, or any active protein which modifies itself or a portion of either a natural or artificially constructed fusion protein in such a way that a peptide selectively binds, with high specificity, only one of the two, modified or unmodified, forms.

As noted above in connection with the technique of Example 3, the technique of the present example is a positive selection technique which can be used to evaluate very large numbers of mutants.

Figure 11:
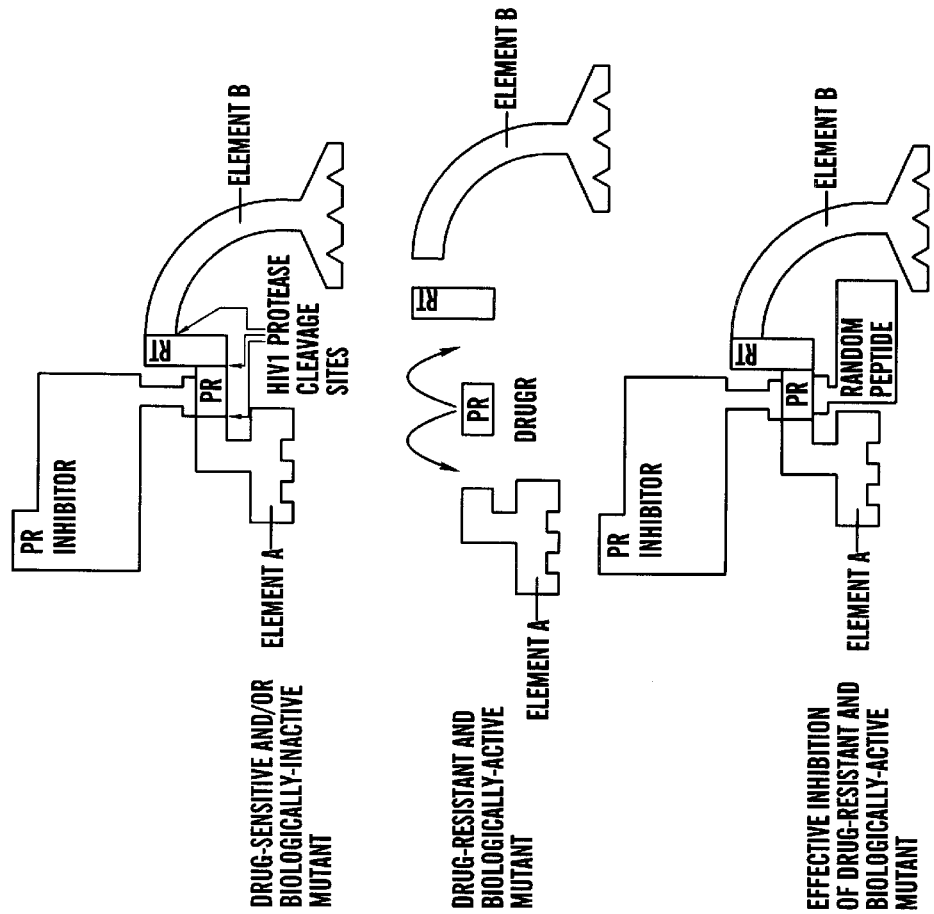
FIG. 11 is a schematic diagram illustrating the selection conditions for identifying auxiliary drugs that are effective against first-generation, drug-resistant, biologically-active mutants determined in accordance with the technique of Example 4.

In addition to being well-suited for identifying drug-resistant mutants, the technique described above can also be used to identify auxiliary drugs effective against the drug-resistant mutants thus identified. This may be done, for example, by generating combinatorial plasmid libraries coding for peptides (e.g., 6–12 amino acids) or nucleotides (e.g., RNA), and then transforming those cells which carry the drug-resistant, biologically-active, mutant forms of the protein with said plasmids. As can be seen in FIG. 11, if a cell expressing a drug-resistant protease takes up a plasmid which encodes an effective inhibitor of the drug-resistant mutant protein, the cell will grow on unsupplemented medium, but not on medium containing 5-FOA and alphaAA. By contrast, if the drug-resistant cell does not take up and/or express a plasmid which encodes an effective inhibitor of the drug-resistant mutant protein, the cell will not grow on unsupplemented medium, but will grow on medium containing 5-FOA and alphaAA. Consequently, in this manner, a large number of potential auxiliary drugs can rapidly be screened. Thereafter, the plasmids from those cells which survive in unsupplemented medium can be isolated and sequenced to determine the identity of the inhibitor.

A similar method can be used to screen for inhibitors from among already existing chemical libraries.

As can readily be appreciated, the above-described procedure can be applied in an unlimited number of iterations to comprehensively define the mutational or evolutionary escape pathway of the protease from inhibitors of present and future drug-resistant forms of the protease.

EXAMPLE 5

The technique of the present example uses a reverse transcriptase assay to monitor protease activity.

Figure 12:
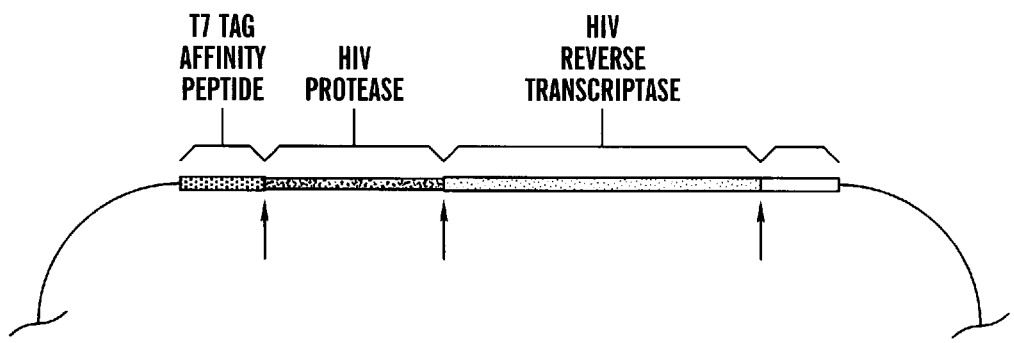
FIG. 12 is a schematic diagram of a portion of the plasmid pL124.23 used in the technique of Example 5.
Figure 13:
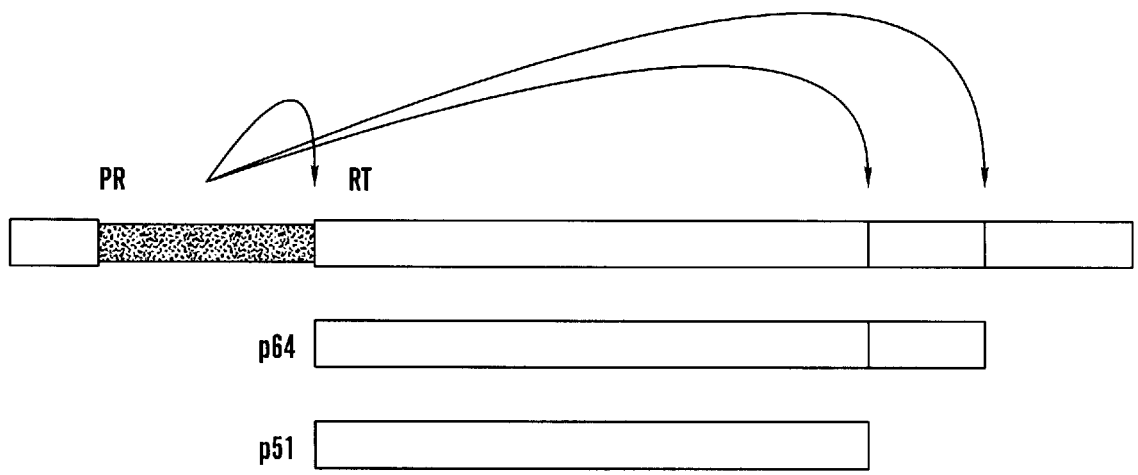
FIG. 13 is a schematic diagram illustrating the protease cleavages necessary for reverse transcriptase activation.

Plasmid pART-2 was digested with Bgl II and Eco RI to obtain a nucleotide sequence coding for a portion of the HIV-1 polyprotein (i.e., the HIV-1 protease protein, the HIV-1 reverse transcriptase protein and a portion of the HIV-1 integrase protein). The isolated 2.3 kb fragment was then inserted into the pTrcHisC plasmid (obtained from Invitrogen, San Diego, Calif.), which had previously been digested with the same restriction enzymes, to yield the plasmid pL124.23. The pL124.23 plasmid contains upstream sequences coding for a series of six histidine residues fused to a gene 10 segment, all of which are in frame with the inserted fragment. An enterokinase cleavage recognition site is also located between gene 10 and the truncated polyprotein. The inserted sequences, as well as the described upstream sequences are all under control of a T7 promoter. The T7 polymerase in the host cell (Top 10, Invitrogen) is inducible with IPTG. FIG. 12 schematically depicts a portion of plasmid pL124.23, as well as a few of the sites where HIV-1 protease digests the polyprotein. (An additional protease cleavage site, which is located within the reverse transcriptase protein and which is necessary to form the two reverse transcriptase subunits p64 and p51 necessary for reverse transcriptase activity, is shown in FIG. 13.) Experiments were performed to demonstrate that the truncated HIV polyprotein was expressed upon induction and that the expressed polyprotein was properly processed by the HIV protease to release active reverse transcriptase heterodimer. Inhibition of the protease by addition of the protease inhibitor, L-735,524, to the growing host cells prior to induction allowed expression of the polyprotein but did not allow processing of the polyprotein.

Figure 14:
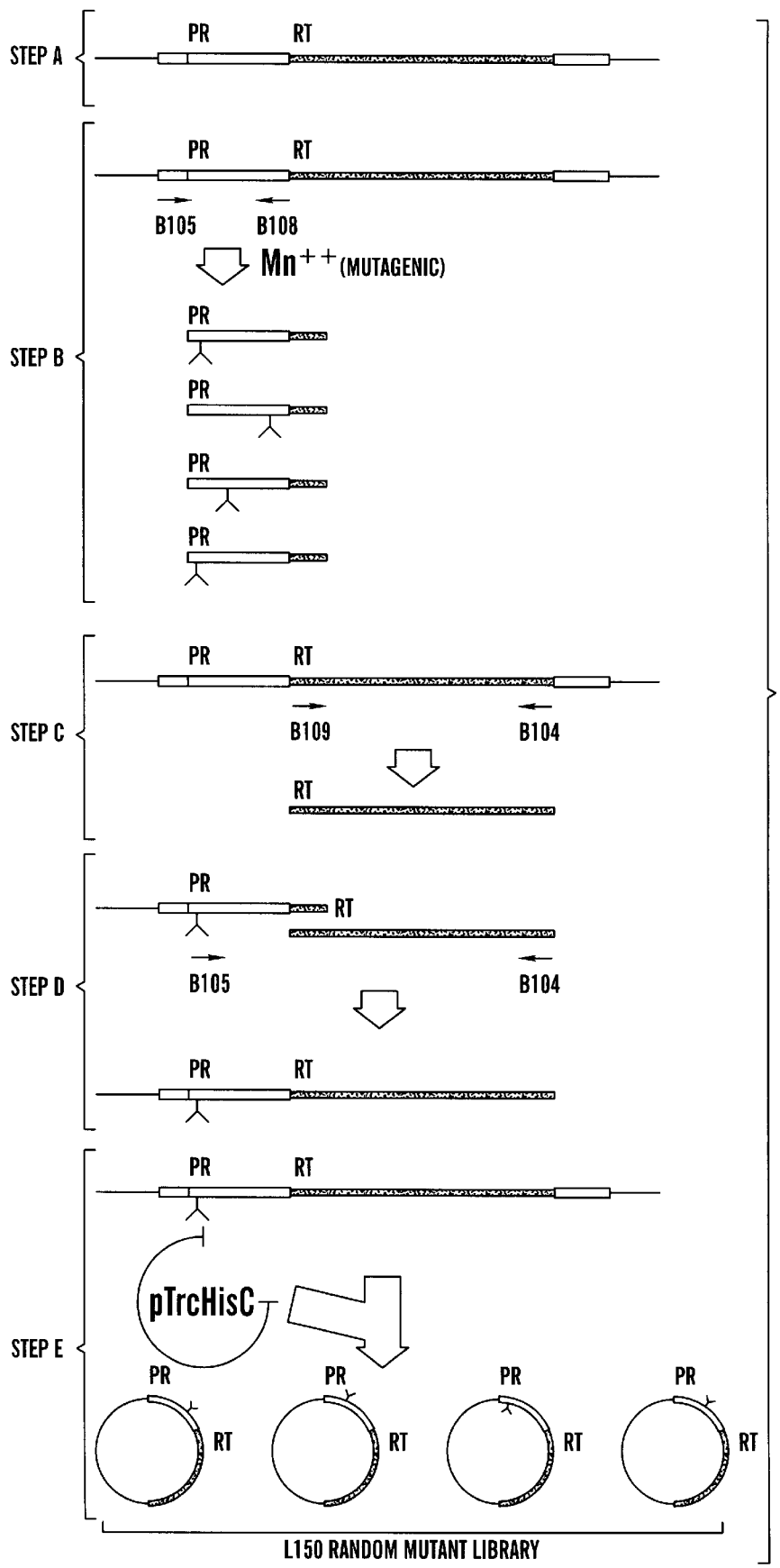
FIG. 14 is a schematic diagram illustrating the sequence of steps used to generate a library of protease mutants using plasmid pL124.23.

Referring now to FIG. 14, there is schematically shown the sequence of steps used to generate a library of protease mutants within the polyprotein using plasmid pL124.23. First, as seen in step A, a fragment of plasmid pL124.23 is shown. Next, as seen in step B, mutagenic PCR (polymerase chain reaction) amplification of the protease-encoding region of the plasmid fragment was achieved using primers B105 and B108, which span the protease. The use of manganese ions, as well as other mutagenic techniques, were used to favor poor fidelity of the Taq polymerase in the PCR amplification. Next, as seen in step C, the reverse transcriptase portion of the fragment was amplified using primers B109 and B104 under conditions favoring high fidelity PCR amplification. Next, as seen in step D, the DNA fragments coding for the mutant protease and reverse transcriptase proteins contained overlapping regions. This allowed PCR joining of these DNA fragments using primers B105 and B104. The reconstructed polyprotein segment codes for a protease mutant, which has an average of two amino acid substitutions, and wild-type reverse transcriptase. Finally, as seen in step E, the library of sequences are ligated into the vector pTrcHisC, which contains DNA that mediates regulated expression of the polyprotein in *E. coli*.

The library of mutant vectors described above was then amplified by transforming *E. coli* with the vectors and allowing the bacteria to grow. Following amplification, the bacteria were distributed into the wells of a microplate. Preferably, only a few cells (more preferably only one cell) were distributed into each well. After the cells were distributed into their respective wells and allowed to grow for several hours, the protease inhibitory drug L-735,524 was added thereto. Expression of the polyprotein was then induced. Where the expressed polyprotein contained a biologically-active, drug-resistant, mutant form of the protease, the polyprotein was cut by the mutant protease to yield active reverse transcriptase heterodimer. By contrast, where the expressed polyprotein contained a biologically-inactive and/or drug-sensitive mutant form of the protease, the polyprotein was not cleaved, and active reverse transcriptase heterodimer was not produced.

Following expression of the polyprotein by the bacterial cells, the polyprotein (either in its intact or cleaved form, depending upon the specific mutant protease involved) was extracted from the bacterial cells into the wells. A colorimetric assay for reverse transcriptase activity (commercially available, for example, from Boehringer Mannheim GmbH) was then used to assay for the presence of active reverse transcriptase in each of the wells, the presence of a dark color in the well indicating the presence of active reverse transcriptase therein (and thereby indicating the presence of biologically-active, drug-resistant protease therein).

Figure 15:
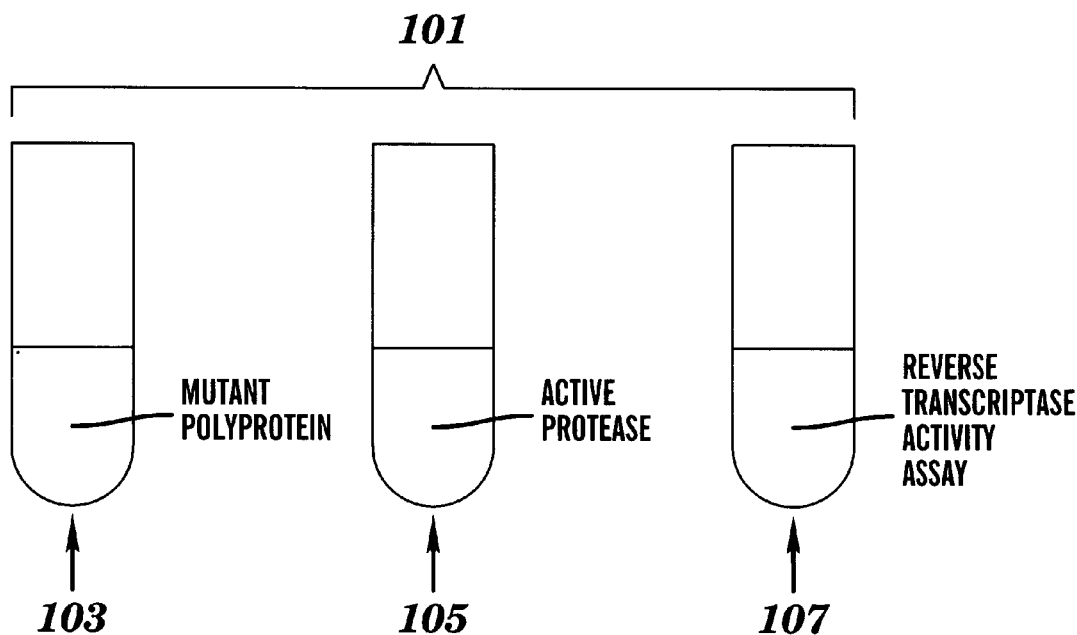
FIG. 15 is a schematic diagram illustrating the components of an assay kit for screening prospective drugs against biologically-active mutant or wild-type forms of the HIV protease.

Referring to FIG. 15, a biologically-active, drug-resistant protease mutant has been identified using the present technique (the protease variant being identified herein as "DLH310"). DNA sequence analysis of DLH310 protease revealed two mutations resulting in the amino acid changes K55N and L90M.

As can readily be appreciated, one highly desirable aspect of the present technique is that it possesses a high degree of authenticity, i.e., the protease mutants are being tested for activity against the actual substrate encountered by them in nature, namely, the cleavage sites of the polyprotein needed to activate reverse transcriptase. The level of authenticity associated with the present technique is to be contrasted with that found in the technique of UK Patent Application 2,276,621, where a single, artificial, cleavage site is all that is required to cleave beta-galactosidase.

It is to be understood that the technique of the present example could readily be used to test potential protease inhibitors against one or more mutant or wild-type forms of the protease.

Figure 16:
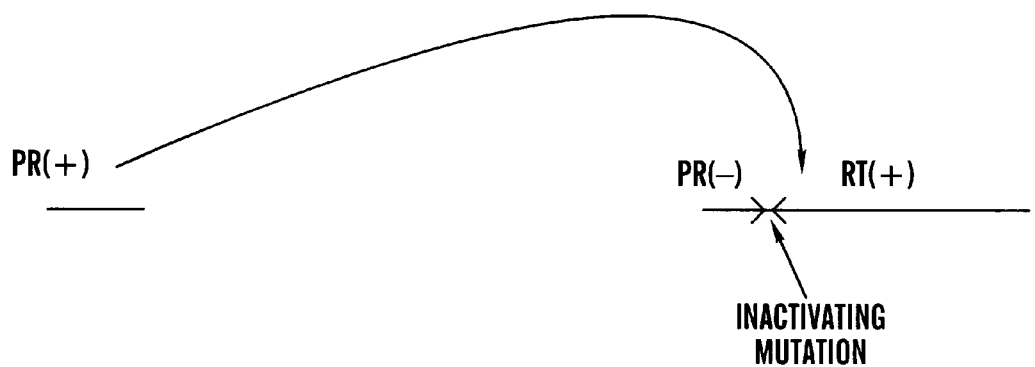
FIG. 16 is a schematic diagram illustrating the transactivation of the reverse transcriptase protein of the mutant polyprotein by the active protease in the assay kit of FIG. 16.

Referring now to FIG. 16, there is shown a schematic diagram of an assay kit for evaluating the efficacy of a prospective drug against a biologically-active mutant or wild-type form of the HIV protease, the assay kit being represented generally by reference numeral 101.

Kit 101 includes a first tube 103, tube 103 containing a mutant form of the HIV-1 polyprotein (the mutant polyprotein including the protease and reverse transcriptase proteins). The mutant polyprotein differs from wild-type polyprotein only in that the mutant polyprotein contains a biologically-inactive form of the protease. The cleavage sites and the reverse transcriptase protein of the mutant polyprotein are indistinguishable from the wild-type polyprotein.

Kit 101 also includes a second tube 105, tube 105 containing a biologically-active form of HIV-1 protease. The biologically-active form of the HIV-1 protease may be the wild-type form of the protease or may be a biologically-active mutant form of the protease. When the HIV-1 protease of tube 105 is combined with the mutant polyprotein of tube 103 in the absence of an effective protease inhibitor, reverse transcriptase is cleaved from the mutant polyprotein by the biologically-active protease in a trans reaction (see FIG. 17).

Kit 101 further includes a second tube 107, tube 107 containing a conventional reverse transcriptase activity assay for detecting the presence of reverse transcriptase activity.

Kit 101 may be used to test a prospective drug for protease inhibitory activity as follows: First, the prospective drug is added to the mutant polyprotein of first tube 103. Next, the biologically-active mutant or wild-type form of the protease is added to the combination of the drug and the mutant polyprotein. Finally, the reverse transcriptase activity assay is exposed to the combination of the drug, mutant polyprotein and active protease. If the prospective drug is effective, reverse transcriptase will not be released from the mutant polyprotein and a negative assay result will follow. If the prospective drug is ineffective, reverse transcriptase will be released from the mutant polyprotein and a positive assay result will follow.

It is to be understood that the principles behind kit 101 can be used to evaluate the sensitivity of clinically-derived HIV protease mutants to prospective drugs. HIV protease mutants can be obtained, for example, from tissue and/or fluid samples or from clinical HIV isolates grown in cell culture. It should be understood, however, that a background level of HIV reverse transcriptase activity may be present when intact virus is used, regardless of whether transactivation of the reverse transcriptase portion of the mutant HIV polyprotein occurs. This is because the intact HIV virus will, in most instances, produce active reverse transcriptase as a result of cleavage of its own polyprotein by the active protease. Notwithstanding the above, assay interference from the background level of reverse transcriptase activity may be reduced by any of a number of methods. According to one method, a nonnucleoside reverse transcriptase inhibitor (NNRTI) is added to the reaction mixture at a level sufficient to counteract the background reverse transcriptase without greatly affecting the reverse transcriptase activated by hydrolysis of the mutant polyprotein by the protease. According to a second method, site directed mutagenesis is used to insert one or more mutations into the reverse transcriptase portion of the mutant polyprotein (i.e., the polyprotein of tube 103) to confer drug resistance to NNRTI's. Mutations Y181C, Y188C and K103N are known to confer NNRTI resistance to HIV-1 reverse transcriptase. (See Richman et al., *Proc. Natl. Acad. Sci., USA,* 88:11241–5 (1991); Richman et al., *Rev. Pharmacol. Toxicol.,* 32:149–64 (1993), and Debyser et al., *Molec. Pharm.,* 365:451–626, all of which are incorporated herein by reference.) In this manner, NNRTI's will inhibit background reverse transcriptase but will not inihibit reverse transcriptase released from the mutant polyprotein by HIV protease. According to a third approach, the reverse transcriptase portion of the mutant polyprotein is labelled with a readily detectable label (e.g., FLAG antigen, which is commercially available from Kodak Scientific Imaging Systems, New Haven, Conn.) which is absorbed to a specific antibody against this label upon hydrolysis of the mutant polyprotein. The antibody, of course, must not be reactive with the polyprotein.

Alternatively, HIV protease mutants may be obtained using standard PCR techniques to amplify the protease portion of HIV RNA or DNA obtained from clinical subjects. The amplified nucleic acid sequences may then be utilized in any of a number of commercially available in vitro translation systems (e.g., rabbit reticulocyte, wheat germ extract, or *E. coli* extracts) to express the active HIV protease. These clinically-derived protease mutants may then be added to the above-described mutant polyprotein in the presence of a prospective protease inhibitory drug and a reverse transcriptase assay to evaluate the efficacy of the prospective drug.

The approach described above can be used to determine the sensitivity of a protease mutant to a variety of prospective drugs in a matter of a few days. This compares quite favorably to the 30 to 40 days typically required to determine the drug sensitivity of HIV clinical isolates using conventional cell-culturing techniques.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A kit for evaluating, in vitro, the efficacy of a drug against a biologically-active mutant or wild-type form of a first protein, the first protein being a protease that is natively expressed as part of a polyprotein with a second protein, the second protein having a biological activity which is catalyzed by cleavage of the polyprotein by the protease, said kit comprising:

(a) a mutant polyprotein, said mutant polyprotein including the second protein, a biologically-inactive mutant form of the protease, and one or more sites cleavable by the biologically-active or wild-type form of the protease in such a way as to activate the second protein;

(b) a biologically-active mutant or wild-type form of the protease which, when combined with the mutant polyprotein in the absence of an effective drug thereagainst, cleaves the mutant polyprotein in such a way as to activate the second protein; and (c) means for detecting the presence of biological activity for the second protein.

2. The kit of claim 1 wherein the mutant polyprotein has the same number and type of cleavage sites needed to cleave the second protein from the mutant polyprotein as are found in the naturally-occurring polyprotein.

3. The kit of claim 1 wherein the protease is HIV protease.

4. The kit of claim 3 wherein the second protein is reverse transcriptase.

5. An in vitro protease assay kit for a protease of the type that is natively expressed as part of a polyprotein with a second protein, the second protein having a biological activity which is catalyzed by cleavage of the polyprotein by the protease, said assay kit comprising:

(a) a mutant polyprotein, said mutant polyprotein including a biologically-inactive mutant form of the protease, said second protein, and one or more sites cleavable by an active form of the protease in such a way as to activate the second protein; and (b) means for detecting the presence of biological activity for the second protein.

6. The in vitro protease assay kit of claim 5 wherein the mutant polyprotein has the same number and type of cleavage sites needed to cleave the second protein from the mutant polyprotein as are found in the naturally-occurring polyprotein.

7. The in vitro protease assay kit of claim 5 wherein the protease is HIV protease.

8. The in vitro protease assay kit of claim 7 wherein the second protein is reverse transcriptase.

9. An in vitro method for evaluating the efficacy of a drug against a biologically active protease chosen from a wild-type protease and a mutant form of a protease, the protease being natively expressed as part of a polyprotein that includes a second protein whose biological activity is dependent upon cleavage of the polyprotein by the protease, said method comprising the steps of:

(a) providing a proteolytically incompetent mutant of the polyprotein that includes (i) a biologically inactive mutant of the protease, (ii) the second protein, and (iii) at least one site cleavable by a biologically active form of the protease to activate the second protein;

(b) adding a drug to be evaluated to the proteolytically incompetent mutant of the polyprotein;

(c) adding the biologically active form of the protease to the product of step (b); and (d) assaying the product of step (c) for the presence of biological activity for the second protein, wherein the absence of biological activity for the second protein indicates that the drug has efficacy against the biologically active form of the protease.

10. The method of claim 9 wherein the proteolytically incompetent mutant of the polyprotein has the same number and type of cleavage sites needed for cleavage by the biologically active form of the protease as are found in the polyprotein.

11. The method of claim 9 wherein the protease is HIV protease.

12. The method of claim 11 wherein the second protein is reverse transcriptase.

13. The method of claim 9 wherein the biologically active protease is a biologically active mutant and said protease is drug-resistant to a second drug, said second drug being a protease inhibitor.

14. The method of claim 9 wherein the biologically active protease is a biologically active mutant and said mutant protease has been identified in a pathogen isolated from a human.

* * * * *